US008722711B2

(12) United States Patent
Yamanoi et al.

(10) Patent No.: US 8,722,711 B2
(45) Date of Patent: May 13, 2014

(54) ACYLBENZENE DERIVATIVE

(75) Inventors: Shigeo Yamanoi, Tokyo (JP); Takahiro Katagiri, Tokyo (JP); Hidenori Namiki, Tokyo (JP); Madoka Hatta, Tokyo (JP); Koji Matsumoto, Tokyo (JP); Kanako Takahashi, Tokyo (JP); Tomomi Yoshitomi, Tokyo (JP); Yuichi Ochiai, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/879,076

(22) PCT Filed: Oct. 13, 2011

(86) PCT No.: PCT/JP2011/073489
§ 371 (c)(1),
(2), (4) Date: Apr. 12, 2013

(87) PCT Pub. No.: WO2012/050151
PCT Pub. Date: Apr. 19, 2012

(65) Prior Publication Data
US 2013/0217733 A1    Aug. 22, 2013

(30) Foreign Application Priority Data

Oct. 14, 2010   (JP) ................................. 2010-231471
Feb. 4, 2011   (JP) ................................. 2011-022325

(51) Int. Cl.
*A61K 31/4245* (2006.01)
*C07D 271/06* (2006.01)

(52) U.S. Cl.
USPC ......................................... 514/364; 548/131

(58) Field of Classification Search
USPC ......................................... 548/131; 514/364
See application file for complete search history.

(56) References Cited

U.S. PATENT DOCUMENTS

| 2009/0054435 A1 | 2/2009 | Imoto |
| 2012/0129832 A1 | 5/2012 | Yamanoi et al. |
| 2012/0129891 A1 | 5/2012 | Yamanoi et al. |

FOREIGN PATENT DOCUMENTS

| WO | 02/16332 A1 | 2/2002 |
| WO | WO 2005/061489 A1 | 7/2005 |
| WO | WO 2007/003960 A1 | 1/2007 |
| WO | WO 2007/003962 A2 | 1/2007 |
| WO | WO 2007/013694 A1 | 2/2007 |
| WO | WO 2007/116229 A1 | 10/2007 |
| WO | WO 2010/112461 A1 | 10/2010 |
| WO | WO 2011/016469 A1 | 2/2011 |
| WO | WO 2011/016470 A1 | 2/2011 |

OTHER PUBLICATIONS

Faucher, et al., "Design, synthesis and evaluation of trifluoromethane sulfonamide derivatives as new potent and selective peroxisome proliferator-activated receptor α agonists," *Bioorganic & Medicinal Chemistry Letters*, vol. 18, pp. 710-715 (2008).
Extended European Search Report issued in European Patent Application No. 11 83 2583 on Jan. 1, 2014, 4 pages.

*Primary Examiner* — Rebecca Anderson
*Assistant Examiner* — Karen Cheng
(74) *Attorney, Agent, or Firm* — Dorsey and Whitney LLP

(57) ABSTRACT

Provided are compounds having an excellent hypoglycemic action and a β cell- or pancreas-protecting action or a pharmaceutically acceptable salt thereof, and a pharmaceutical composition having an excellent therapeutic effect and/or prophylactic effect on type 1 diabetes, type 2 diabetes, and the like, which cause an increase in the blood sugar level due to abnormal sugar metabolism. A compound represented by general formula (I), or a pharmaceutically acceptable salt thereof, is disclosed.

[Chemical Formula 1]

27 Claims, No Drawings

ACYLBENZENE DERIVATIVE

This application is a national stage application under 35 U.S.C. §371 of International Application No. PCT/JP2011/073489, filed Oct. 13, 2011, entitled "Acylbenzene Derivative," which claims priority to Japanese Patent Application No. 2010-231471, filed Oct.14, 2010, and to Japanese Patent Application No. 2011-022325, filed Feb. 4, 2011.

TECHNICAL FIELD

The present invention relates to a novel acylbenzene derivative having a hypoglycemic action and/or a β cell- or pancreas-protecting action, or to a pharmaceutically acceptable salt thereof, and a pharmaceutical composition containing these as active ingredients.

BACKGROUND ART

Diabetes mellitus is a metabolic disease primarily characterized by a chronic hyperglycemic state due to a lack of insulin action. The treatment of diabetes is generally by drug therapy together with diet therapy and exercise therapy. Examples of oral hypoglycemic agents in use, which are a class of therapeutic drugs for diabetes, include biguanide agents and thiazolidinedione agents that improve insulin resistance; sulfonylurea agents and glinide drugs that promote insulin secretion from pancreatic β cells; and α-glucosidase inhibitors that inhibit sugar absorption.

However, it is reported that biguanide agents have adverse side effects such as digestive symptoms and lactic acidosis; thiazolidinedione agents have adverse side effects such as weight gain and edema; sulfonylurea agents and glinide drugs have adverse side effects such as hypoglycemia or secondary failure due to long-term use; and α-glucosidase inhibitors have adverse side effects such as diarrhea. Therefore, development of an oral hypoglycemic agent which can address such problems is desired.

Furthermore, in recent years, piperidine compounds have been developed as oral hypoglycemic agents having new structures (see, for example, Patent Literature 1 to 4). Still further, oxadiazole compounds have been disclosed (see, for example, Patent Literature 5 or 6).

CITATION LIST

Patent Literature

Patent Literature 1: WO 07/116,229
Patent Literature 2: WO 07/003,960
Patent Literature 3: WO 07/003,962
Patent Literature 4: WO 05/061489
Patent Literature 5: WO 11/016,469
Patent Literature 6: WO 11/016,470

SUMMARY OF THE INVENTION

Problems to be Solved by the Invention

However, the piperidine compounds have a problem in that a sufficient hypoglycemic action and a β cell- or pancreas-protecting action cannot be easily obtained. Thus, an object of the present invention is to provide compounds which have a new structure that is neither described nor suggested in the above patent literature and have an excellent hypoglycemic action, and a β cell- or pancreas-protecting action, or a pharmaceutically acceptable salt thereof; a pharmaceutical composition having an excellent therapeutic effect and/or prophylactic effect on type 1 diabetes, type 2 diabetes and the like, which cause an increase in the blood sugar level due to abnormal sugar metabolism; and a pharmaceutical composition having a β cell- or pancreas-protecting action.

Means for Solving the Problems

The present invention provides:
(1) a compound represented by general formula (I):

[Chemical Formula 1]

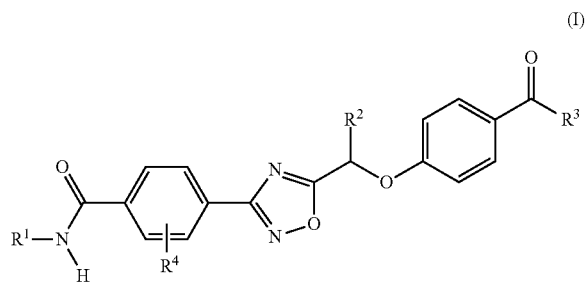

(I)

wherein $R^1$ represents a hydroxy C1-C6 alkyl group or a hydroxy C3-C6 cycloalkyl group, each of which may be substituted with 1 to 3 substituents selected from substituent subgroup α,
substituent subgroup α is a group consisting of a hydroxyl group and a carbamoyl group,
$R^2$ represents a methyl group or an ethyl group,
$R^3$ represents a C1-C6 alkyl group or a C3-C6 cycloalkyl group, each of which may be substituted with 1 to 3 halogen atoms, and
$R^4$ represents a halogen atom;
or a pharmaceutically acceptable salt thereof.
(2) the compound as set forth in item (1), wherein R1 represents a hydroxy C1-C3 alkyl group or a hydroxy C3-C4 cycloalkyl group, each of which may be substituted with 1 to 3 substituents selected from substituent subgroup α;
(3) the compound as set forth in item (1), wherein $R^1$ represents a hydroxyethyl group, a hydroxypropyl group, a hydroxyisopropyl group, or a hydroxycyclopentyl group, each of which may be substituted with one substituent selected from substituent subgroup α;
(4) the compound as set forth in any one of items (1) to (3), wherein R3 represents a C1-C4 alkyl group or a C3-C4 cycloalkyl group, each of which may be substituted with 1 to 3 halogen atoms;
(5) the compound as set forth in any one of items (1) to (3), wherein $R^3$ represents an isopropyl group, a tert-butyl group, a cyclopropyl group, or a cyclobutyl group, each of which may be substituted with one halogen atom;
(6) the compound as set forth in any one of items (1) to (5), wherein $R^4$ represents a fluorine atom;
(7) a compound selected from the group consisting of the following compounds:
4-(5-{(1R)-1-[4-(cyclopropylcarbonyl)phenoxy]propyl}-1,2,4-oxadiazol-3-yl)-N-[(2S)-2,3-dihydroxypropyl]-2-fluorobenzamide,
N-[(1S)-2-amino-1-(hydroxymethyl)-2-oxoethyl]-4-(5-{(1R)-1-[4-(cyclopropylcarbonyl)phenoxy]propyl}-1,2,4-oxadiazol-3-yl)-2-fluorobenzamide,
4-(5-{(1R)-1-[4-(cyclopropylcarbonyl)phenoxy]propyl}-1,2,4-oxadiazol-3-yl)-2-fluoro-N-[(1R)-2-hydroxy-1-methylethyl]benzamide, 4-(5-{(1R)-1-[4-(cyclopropylcarbonyl)phenoxy]propyl}-1,2,4-oxadiazol-3-yl)-2-fluoro-N-[(1S)-2-hydroxy-1-methylethyl]benzamide, 4-(5-{(1R)-1-[4-(cyclopropylcarbonyl)phenoxy]propyl}-1,2,4-oxadiazol-3-yl)-N-[(2R)-2,3-dihydroxypropyl]-2-fluorobenzamide, 4-(5-{(1R)-1-[4-(cyclopropylcarbonyl)phenoxy]propyl}-1,2,4-oxadiazol-3-yl)-2-fluoro-N-[2-hydroxy-1-(hydroxymethyl)ethyl]benzamide, 4-(5-{(1R)-1-[4-(cyclopropylcarbonyl)phenoxy]ethyl}-1,2,4-oxadiazol-3-yl)-2-fluoro-N-[2-hydroxy-1-(hydroxymethyl)ethyl]benzamide, 4-(5-{(1R)-1-[4-(cyclopropylcarbonyl)phenoxy]ethyl}-1,2,4-oxadiazol-3-yl)-2-fluoro-N-[(1S)-2-hydroxy-1-methylethyl]benzamide, 4-(5-{(1R)-1-[4-(cyclopropylcarbonyl)phenoxy]ethyl}-1,2,4-oxadiazol-3-yl)-2-fluoro-N-[(1R,2R)-2-hydroxycyclopentyl]benzamide, 4-(5-{(1R)-1-[4-(cyclopropylcarbonyl)phenoxy]ethyl}-1,2,4-oxadiazol-3-yl)-2-fluoro-N-[(1R)-2-hydroxy-1-methylethyl]benzamide, 4-(5-{(1R)-1-[4-(cyclopropylcarbonyl)phenoxy]ethyl}-1,2,4-oxadiazol-3-yl)-2-fluoro-N-[(1S,2S)-2-hydroxycyclopentyl]benzamide, 4-(5-{(1R)-1-[4-(2,2-dimethylpropanoyl)phenoxy]propyl}-1,2,4-oxadiazol-3-yl)-2-fluoro-N-[2-hydroxy-1-(hydroxymethyl)ethyl]benzamide, 4-(5-{(1R)-1-[4-(cyclobutylcarbonyl)phenoxy]propyl}-1,2,4-oxadiazol-3-yl)-2-fluoro-N-[2-hydroxy-1-(hydroxymethyl)ethyl]benzamide, 2-fluoro-4-{5-[(1R)-1-[(4-[(1-fluorocyclopropyl)carbonyl]phenoxy}propyl]-1,2,4-oxadiazol-3-yl]-N-[2-hydroxy-1-(hydroxymethyl)ethyl]benzamide, 2-fluoro-N-[(1R)-2-hydroxy-1-methylethyl]-4-{5-[(1R)-1-(4-isobutyrylphenoxy)propyl]-1,2,4-oxadiazol-3-yl}benzamide, and 2-fluoro-N-[2-hydroxy-1-(hydroxymethyl)ethyl]-4-{5-[(1R)-1-(isobutyrylphenoxy)propyl]-1,2,4-oxadiazol-3-yl}benzamide;

(8) a pharmaceutical composition containing, as an active ingredient, the compound as set forth in any one of items (1) to (7), or a pharmaceutically acceptable salt thereof;

(9) the pharmaceutical composition as set forth in item (8), for treating type 1 diabetes, type 2 diabetes, or obesity;

(10) the pharmaceutical composition as set forth in item (8), for protecting β cells or the pancreas;

(11) use of the compound as set forth in any one of items (1) to (7) or a pharmaceutically acceptable salt thereof, for preparing a pharmaceutical composition;

(12) a method for treating a disease, the method including administering to a mammal the compound as set forth in any one of items (1) to (7) or a pharmaceutically acceptable salt thereof; and

(13) the method as set forth in item (12), wherein the mammal is a human being.

Effects of the Invention

According to the present invention, there is provided an acylbenzene derivative having an excellent hypoglycemic action, and a β cell- or pancreas-protecting action, or a pharmaceutically acceptable salt thereof, a pharmaceutical composition having an excellent therapeutic effect and/or prophylactic effect on type 1 diabetes, type 2 diabetes and the like, which cause an increase in the blood sugar level, and a pharmaceutical composition having a β cell- or pancreas-protecting effect.

Best Modes for Carrying Out the Invention

A "C1-C6 alkyl group" as used in the present specification means a linear or branched alkyl group having 1 to 6 carbon atoms. Specific examples include a methyl group, an ethyl group, a propyl group, an isopropyl group, a butyl group, an isobutyl group, a sec-butyl group, a tert-butyl group, a pentyl group, a 1,2-dimethyl-propyl group, an isopentyl group, a hexyl group, and an isohexyl group.

A "C3-C6 cycloalkyl group" as used in the present specification means a saturated cyclic hydrocarbon group having 3 to 6 carbon atoms, and examples include a cyclopropyl group, a cyclobutyl group, a cyclopentyl group, and a cyclohexyl group.

A "hydroxy C1-C6 alkyl group" as used in the present specification means a group obtained by substituting a hydrogen atom of a "C1-C6 alkyl group" with a hydroxyl group. Specific examples include hydroxymethyl, 2-hydroxyethyl, 4-hydroxybutyl, 5-hydroxypentyl, and 6-hydroxyhexyl groups.

A "hydroxy C3-C6 cycloalkyl group" as used in the present specification means a group obtained by substituting a hydrogen atom of a "C3-C6 cycloalkyl group" with a hydroxyl group. Specific examples include a hydroxycyclopropyl group, a hydroxycyclobutyl group, a 2-hydroxycyclopentyl group, and a hydroxycyclohexyl group.

A "halogen atom" as used in the present specification means a fluorine atom, a chlorine atom, a bromine atom, or an iodine atom.

A "pharmaceutically acceptable salt" as used in the present specification means a salt formed by allowing the compound of the present invention to react with an acid or a base.

Examples of the salt include hydrohalogenic acid salts such as hydrofluorides, hydrochlorides, hydrobromides, and hydroiodides; inorganic acid salts such as hydrochlorides, nitrates, perchlorates, sulfates and phosphates; lower alkanesulfonic acid salts such as methanesulfonates, trifluoromethanesulfonates, and ethanesulfonates; arylsulfonic acid salts such as benzenesulfonates, and p-toluenesulfonates; organic acid salts such as acetates, malates, fumarates, succinates, citrates, ascorbates, tartrates, oxalates, and maleates; alkali metal salts such as sodium salts, potassium salts, and lithium salts; alkaline earth metal salts such as calcium salts and magnesium salts; metal salts such as aluminum salts and iron salts; inorganic salts such as ammonium salts; amine salts including organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, and tris(hydroxymethyl)aminomethane salts; and amino acid salts such as glycine salts, lysine salts, arginine salts, ornithine salts, glutamates, and aspartates.

The compound of the present invention absorbs water when, for example, left to stand in the atmosphere, so that the adsorbed water can adhere to the compound and a hydrate may be formed. Therefore, such a hydrate is also included in the concept of the salt of the present invention.

Since the compound of the present invention may have asymmetric carbon atoms in the molecule, the compound has optical isomers. These isomers and mixtures of these isomers are all represented by a single formula, that is, the general formula (I). Therefore, the present invention encompasses all of the optical isomers of the compound represented by the general formula (I), and mixtures of these optical isomers at any ratios. Such an optical isomer can be produced by, for example, using raw materials having optical activity instead of the raw materials used in the production methods, Reference Examples and Examples that will be described below, or can be obtained by subjecting a compound that has been produced by making reference to the production methods, Reference Examples, Examples and the like that will be described below, to an optical resolution method that is known in the pertinent art, for example, a diastereomer method, an enzymatic reaction method, or an optical resolution method based on chromatography.

The present invention may also encompass compounds in which one or more of the atoms constituting the compound represented by the general formula (I) have been substituted with isotopes of the atoms. Isotopes include the two classes of radioactive isotopes and stable isotopes, and examples of the isotopes include, for example, isotopes of hydrogen ($^2$H and $^3$H), isotopes of carbon ($^{11}$C, $^{13}$C and $^{14}$C), isotopes of nitrogen ($^{13}$N and $^{15}$N), isotopes of oxygen (150, 170 and 180), and isotopes of fluorine ($^{18}$F). A composition containing a compound labeled with an isotope is useful as, for example, a therapeutic agent, a prophylactic agent, a research reagent, an assay reagent, a diagnostic agent, or an in vivo diagnostic imaging agent. Compounds labeled with isotopes and mixtures of compounds labeled with isotopes at any ratios are all included in the present invention. A compound labeled with an isotope can be produced by a method that is known in the pertinent art, for example, using raw materials labeled with isotopes instead of the raw materials used in the production methods that will be described below.

The present invention may also encompass prodrugs of the compound represented by the general formula (I). A prodrug is a derivative of the compound represented by the general formula (I), and means a compound which is enzymatically or chemically converted to the compound of the present invention in the living body.

Examples of the prodrug include compounds in which an amino group in the molecule has been acylated, alkylated or phosphorylated; compounds in which a carboxyl group in the molecule has been esterified or amidated; and compounds in which a hydroxyl group in the molecule has been acylated, alkylated or phosphorylated (see, for example, Povl Krogsgaard-Larsen, et al., "A Textbook of Drug Design and Development", Second Edition, Harwood Academic Publishers, 1996, pp. 351-385). Such a prodrug can be produced from the compound represented by the general formula (I) by a method known in the pertinent art.

$R^1$ preferably represents a hydroxy C1-C3 alkyl group or a C3-C4 cycloalkyl group, each of which may be substituted with 1 to 3 substituents selected from substituent subgroup α; more preferably represents a hydroxyethyl group, a hydroxypropyl group, a hydroxyisopropyl group, or a hydroxycyclopentyl group, each of which may be substituted with one substituent selected from substituent subgroup □; and even more preferably represents a 2,3-dihydroxypropyl group, a 2-hydroxy-1-hydroxymethylethyl group, a 1-carbamoyl-2-hydroxyethyl group, a 2-hydroxy-1-methylethyl group, or a 2-hydroxycyclopentyl group.

$R^2$ preferably represents an ethyl group.

$R^3$ preferably represents a C1-C4 alkyl group or a C3-C4 cycloalkyl group, each of which may be substituted with 1 to 3 halogen atoms; more preferably represents an isopropyl group, a tert-butyl group, a cyclopropyl group, or a cyclobutyl group, each of which may be substituted with 1 to 3 halogen atoms; and even more preferably represents an isopropyl group, a tert-butyl group, a cyclopropyl group, a 1-fluorocyclopropyl group, or a cyclobutyl group.

$R^4$ preferably represents a fluorine atom.

A preferred combination of $R^1$, $R^2$, $R^3$ and $R^4$ in the general formula (I) is a combination in which $R^1$ is a hydroxy C1-C3 alkyl group or a C3-C4 cycloalkyl group, each of which may be substituted with 1 to 3 substituents selected from substituent subgroup α; $R^2$ is an ethyl group; $R^3$ is a C1-C4 alkyl group or a C3-C4 cycloalkyl group, each of which may be substituted with 1 to 3 halogen atoms, and $R^4$ represents a fluorine atom.

A more preferred combination is a combination in which $R^1$ is a hydroxyethyl group, a hydroxypropyl group, a hydroxyisopropyl group, or a hydroxycyclopentyl group, each of which may be substituted with one substituent selected from substituent subgroup α; $R^2$ is an ethyl group; $R^3$ is an isopropyl group, a tert-butyl group, a cyclopropyl group, or a cyclobutyl group, each of which may be substituted with 1 to 3 halogen atoms; and $R^4$ represents a fluorine atom.

An even more preferred combination is a combination in which $R^1$ is a 2,3-dihydroxypropyl group, a 2-hydroxy-1-hydroxymethylethyl group, a 1-carbamoyl-2-hydroxyethyl group, a 2-hydroxy-1-methylethyl group, or a 2-hydroxycyclopentyl group; $R^2$ is an ethyl group; $R^3$ is an isopropyl group, a tert-butyl group, a cyclopropyl group, a 1-fluorocyclopropyl group, or a cyclobutyl group; and $R^4$ represents a fluorine atom.

The compound of the present invention can be produced by, for example, the following methods In the reactions of the various steps of the methods described below, when a compound serving as a reaction substrate has a group which inhibits the intended reaction (for example, an amino group, a hydroxyl group, or a carboxyl group), introduction of a protective group to such a group and removal of the introduced protective group may be carried out as necessary. There are no particular limitations on these protective groups as long as they are conventionally used protective groups, but examples include those protective groups described in T. H. Greene, P. G. Wuts, Protective Groups in Organic Synthesis. Third Edition, 1999, John Wiley & Sons, Inc., or the like. The reaction for introducing these protective groups and the reaction for removing the protective groups can be carried out according to routine methods, such as the methods described in the literature mentioned above.

[Chemical Formula 2]

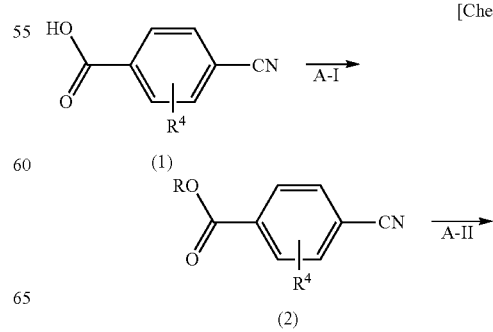

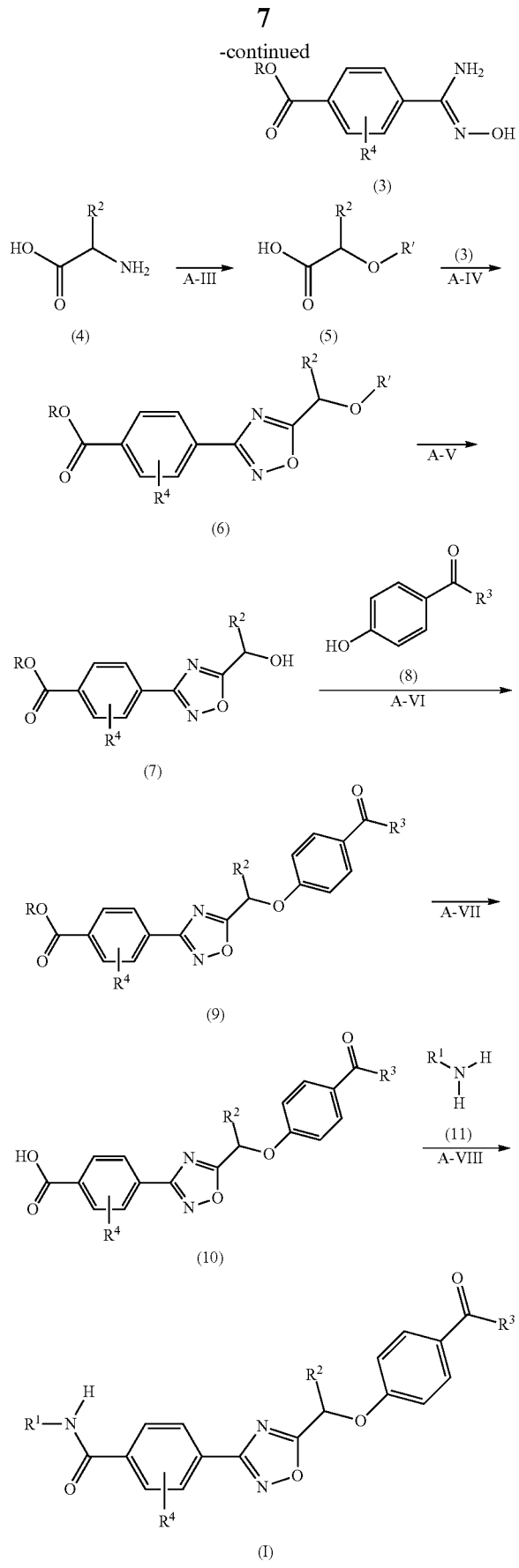

wherein R and R' represent a protective group of a carboxyl group and a protective group of a hydroxyl group, respectively, and $R^1$, $R^2$, $R^3$, and $R^4$ respectively have the same meanings as defined above.

Step A-I is a step for producing a compound (2) by inserting a protective group R in a carboxyl group of a compound (1). The solvent, reagent, reaction temperature, and reaction time used therein can be selected appropriately, for example, by making reference to T. H. Greene, P. G. Wuts, Protective Groups in Organic Synthesis. Third Edition, 1999, John Wiley & Sons, Inc., and the like.

Step A-II is a step for producing a compound (3) by allowing a compound (2) to react with hydroxylamine.

Examples of the solvent used therein include methanol, ethanol, butanol, toluene, dichloromethane, dimethylformamide (DMF), tetrahydrofuran (THF), and dimethylsulfoxide, and a preferred one is ethanol or THF.

Examples of the hydroxylamine used therein include a 50 w/w % aqueous solution of hydroxylamine and hydroxylamine hydrochloride, and a preferred example is a 50 w/w % aqueous solution of hydroxylamine.

The reaction temperature is 0° C. to 150° C., and preferably 70° C. to 90° C. The reaction time is 30 minutes to 24 hours, and preferably 2 to 4 hours.

When a post-treatment is needed, for example, a post-treatment may be carried out according to the following procedure. The reaction mixture is cooled to room temperature, subsequently the solvent is distilled off under reduced pressure, and the resulting residue is washed with water.

Step A-III is a step for producing a compound (5) by allowing a compound (4) to react with a nitrite ester and carboxylic acid.

Examples of the nitrite ester used therein include tert-butyl nitrite, and n-butyl nitrite, and a preferred one is tert-butyl nitrite.

Examples of the carboxylic acid used therein include, for example, acetic acid, and propionic acid, and a preferred one is acetic acid.

The reaction temperature is −20° C. to 100° C., and preferably 0° C. to 70° C. The reaction time is 1 to 24 hours, and preferably 2 to 4 hours.

When a post-treatment is needed, for example, post-treatment may be carried out according to the following procedure. The reaction mixture is cooled to room temperature, and then the solvent is distilled off under reduced pressure. Water is added to the resulting residue, and the product is extracted using an organic solvent such as ethyl acetate. The organic layer thus obtained is dried over a desiccant such as sodium sulfate. After the insoluble matter is removed, the solvent is distilled off under reduced pressure.

Step A-IV is a step for producing a compound (6) by allowing a compound (3) obtained in A-II step to react with a compound (5) obtained in A-III step in the presence of a condensing agent.

Examples of the solvent used therein include, for example, dichloromethane, tetrahydrofuran, 1,4-dioxane, DMF, dimethylacetamide, a preferred one is dichloromethane or DMF, and a more preferred one is DMF.

The condensing agent used therein includes (i) carbodiimides such as 1,3-dicyclohexylcarbodiimide, 1,3-diisopropylcarbodiimide, and 1-ethyl-3-(3-dimethylaminopropyl)carbodiimide (WSC), and combinations of these carbodiimides and N-hydroxy compounds such as 1-hydroxybenzotriazole, 1-hydroxy-7-azabenzotriazole, and N-hydroxysuccinimide, and (ii) imidazoles such as 1,1'-carbonyldiimidazole (CDI), and a preferred one is a combination of WSC and 1-hydroxybenzotriazole.

The reaction temperature is 0° C. to 200° C., and preferably 20° C. to 120° C. The reaction time is 30 minutes to 24 hours, and preferably 2 to 4 hours.

When a post-treatment is needed, for example, a post-treatment may be carried out according to the following procedure. Water is added to the reaction mixture, and the product is extracted using an organic solvent such as ethyl acetate. The organic layer thus obtained is dried over a desiccant such as sodium sulfate. After the insoluble matter is removed, the solvent is distilled off under reduced pressure, and the residue is purified by silica gel chromatography.

Step A-V is a step for producing a compound (7) by removing a protective group R' from the compound (6) obtained in step A-IV.

Examples of the solvent used therein include methanol, ethanol, 2-propanol, and n-butanol, and a preferred one is ethanol.

Examples of the reagent used therein include potassium carbonate, sodium carbonate, potassium hydroxide, and sodium hydroxide, and a preferred one is potassium carbonate.

The reaction temperature is −30° C. to 100° C., and preferably −20° C. to 20° C. The reaction time is 10 to 120 minutes, and preferably 20 to 50 minutes.

When a post-treatment is needed, for example, a post-treatment may be carried out according to the following procedure. An acid such as hydrochloric acid is added to the reaction mixture to make the reaction mixture slightly acidic or neutral, and the product is extracted using an organic solvent such as ethyl acetate. The organic layer thus obtained is dried over a desiccant such as sodium sulfate. After the insoluble matter is removed, the solvent is distilled off under reduced pressure, and the residue is purified by silica gel chromatography.

Step A-VI is a step for producing a compound (9) by allowing the compound (7) obtained in step A-V to react with the compound (8).

Examples of the solvent used therein include THF, dichloromethane, acetonitrile, and toluene, and a preferred one is THF.

Examples of the reagent used therein include (i) combinations of azodicarboxylic acid esters such as diethyl azodicarboxylate and di-tert-butyl azodicarboxylate, and phosphines such as triphenylphosphine and tributylphosphine, and (ii) (cyanomethylene)phosphoranes such as (cyanomethylene)trimethylphosphorane and (cyanomethylene)tributylphosphorane, and a preferred one is a combination of di-tert-butyl azodicarboxylate and triphenylphosphine.

The reaction temperature is −20° C. to 100° C., and preferably 0° C. to 40° C. The reaction time is 10 minutes to 6 hours, and preferably 30 minutes to 2 hours.

When a post-treatment is needed, for example, a post-treatment may be carried out according to the following procedure. After the solvent is distilled off under reduced pressure, water is added to the reaction mixture, and the product is extracted using an organic solvent such as ethyl acetate. The organic layer thus obtained is dried over a desiccant such as sodium sulfate. After the insoluble matter is removed, the solvent is distilled off under reduced pressure, and the residue is purified by silica gel chromatography.

Step A-VII is a step for producing a compound (10) by removing a protective group R from the compound (9) obtained in step A-VI.

Examples of the solvent used therein include dichloromethane, and ethyl acetate, and a preferred one is dichloromethane.

Examples of the reagent used therein include hydrogen chloride, and trifluoroacetic acid, and a preferred one is trifluoroacetic acid.

The reaction temperature is −20° C. to 60° C., and preferably 10° C. to 30° C. The reaction time is 10 minutes to 6 hours, and preferably 20 minutes to 2 hours.

When a post-treatment is needed, for example, a post-treatment may be carried out according to the following procedure. The solvent is distilled off under reduced pressure, and the resulting residue is washed with isopropyl ether.

Step A-VIII is a step for producing the compound (1) of the present invention by allowing the compound (10) obtained in step A-VII to react with an amine compound (11) in the presence of a condensing agent.

Examples of the solvent used therein include dichloromethane, THF, 1,4-dioxane, DMF, and dimethylacetamide, a preferred one is dichloromethane or DMF, and a more preferred one is DMF.

The condensing agent used therein is not particularly limited as long as it is an agent used in amidation reactions, and the condensing agents described in R. C. Larock, Comprehensive Organic Transformations, Second Edition, 1999, John Wiley & Sons, Inc., and the like may be used. Specific examples include (i) phosphoric acid esters such as diethylphosphoryl cyanide; (ii) carbodiimides such as 1,3-dicyclohexylcarbodiimide, 1,3-diisopropylcarbodiimide, and WSC, and combinations of these carbodiimides and N-hydroxy compounds such as 1-hydroxybenzotriazole; (iii) imidazoles such as CDI; (iv) 4-(4,6-dimethoxy-1,3,5-triazin-2-yl)-4-methylmorpholinium chloride (DMT-MM); and (v) phosphates such as O-(7-azabenzotriazol-1-yl)-N,N,N',N'-tetramethyluronium hexafluorophosphate (HATU), and O-benzotriazol-1-yl-N,N,N',N'-tetramethyluronium hexafluorophosphate (HBTU). A preferred one is a combination of WSC and 1-hydroxybenzotriazole.

The reaction temperature is 0° C. to 100° C., and preferably 0° C. to 50° C. The reaction time is 30 minutes to 96 hours, and preferably 1 to 12 hours.

When a post-treatment is needed, for example, a post-treatment may be carried out according to the following procedure. Water is added to the reaction mixture, and then the product is extracted using an organic solvent such as ethyl acetate. The organic layer thus obtained is washed with water, brine and the like, and is dried over a desiccant such as sodium sulfate. The solvent is distilled off under reduced pressure, and the residue is purified by silica gel chromatography.

The compound of the present invention can be produced by using the methods described above, and can also be easily produced from known compounds according to the Reference Examples and Examples that will be described below.

The compound of the present invention or a pharmaceutically acceptable salt thereof obtained by the methods described above has an excellent hypoglycemic action, and can therefore be used as an active ingredient of a pharmaceutical composition that can be used in the treatment and/or prevention of type 1 diabetes, type 2 diabetes, gestational diabetes, hyperglycemia due to other factors, impaired glucose tolerance (IGT), obesity, diabetes-associated diseases (for example, hyperlipidemia, hypercholesterolemia, abnormal lipid metabolism, hypertension, fatty liver, metabolic syndrome, edema, heart failure, angina pectoris, myocardial infarction, arteriosclerosis, hyperuricemia, and gout), or diabetic complications (for example, retinosis, kidney failure, neuropathy, cataract, gangrenous leg, infections, and ketosis).

Furthermore, the compound of the present invention or a pharmaceutically acceptable salt thereof has an excellent β cell- or pancreas-protecting action, and can therefore be used as an active ingredient of a pharmaceutical composition that can be used to protect β cells or the pancreas.

The compound of the present invention can also be used in combination with a therapeutic drug for diabetes other than the compound of the present invention, a therapeutic drug for diabetic complications, a therapeutic drug for hyperlipidemia, a therapeutic drug for hypertension, and the like.

When a pharmaceutical composition containing the compound of the present invention or a pharmaceutically acceptable salt thereof is administered to a mammal (for example, a human being, a horse, a cow or a pig; preferably a human being), the pharmaceutical composition can be administered systemically or topically, and orally or parenterally.

Appropriate dosage forms of the pharmaceutical composition of the present invention can be selected in accordance with the administration mode. The pharmaceutical composition of the present invention can be prepared according to the preparation methods for various conventionally used formulations.

Examples of the dosage form of the pharmaceutical composition for oral use include tablets, pills, powders, granules, capsules, liquids, suspensions, emulsions, syrups, and elixirs. Pharmaceutical compositions of such dosage forms can be prepared according to conventional methods, by appropriately selecting as necessary, excipients, binders, disintegrants, lubricating agents, swelling agents, swelling aids, coating agents, plasticizers, stabilizers, antiseptics, antioxidants, colorants, dissolution aids, suspending agents, emulsifiers, sweeteners, preservatives, buffers, diluents, wetting agents and the like, which are conventionally used as additives.

Examples of the dosage forms of a pharmaceutical composition for parenteral use include injections, ointments, gels, creams, poultices, patches, aerosols, inhalants, sprays, eye drops, nose drops, and suppositories. Pharmaceutical compositions of such dosage forms can be prepared according to conventional methods, by appropriately selecting as necessary, stabilizers, antiseptics, dissolution aids, moisturizers, preservatives, antioxidants, fragrances, gelling agents, neutralizing agents, buffers, isotonic agents, surfactants, colorants, buffering agents, thickeners, wetting agents, fillers, absorption promoting agents, suspending agents, binders, and the like, which are conventionally used as additives.

The administration amount of the compound of the present invention or a pharmaceutically acceptable salt thereof may vary with the symptoms, age, body weight or the like. However, in the case of oral administration, the compound or the salt is administered once or several times a day, in an amount of 1 to 2000 mg, and preferably 1 to 400 mg, in terms of the compound, per dose for an adult; and in the case of parenteral administration, the compound or the salt is administered once or several times a day, in an amount of 0.01 to 500 mg, and preferably 0.1 to 300 mg, in terms of the compound, per dose for an adult.

Hereinafter, the present invention will be described in more detail by way of Reference Examples, Examples, Production Examples, a Formulation Example and Test Examples, but the scope of the present invention is not intended to be limited to these.

EXAMPLES

Reference Example 1 tert-Butyl 4-cyano-2-fluorobenzoate

[Chemical Formula 3]

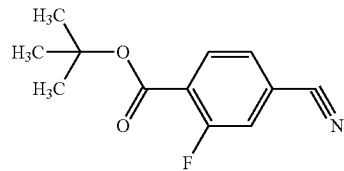

Di-tert-butyl dicarbonate (145.4 g, 666 mmol), and 4-dimethylaminopyridine (7.40 g, 60.6 mmol) were added to a tert-butyl alcohol (1000 mL)-tetrahydrofuran (500 mL) solution of 4-cyano-2-fluorobenzoate (100.0 g, 606 mmol), and the mixture was stirred at 60° C. for 3 hours. The reaction mixture was cooled to room temperature, and the insoluble material was removed by filtration through Celite. The solvent was distilled off under reduced pressure. Thus, a crude product of the title compound was obtained.

Reference Example 2 tert-Butyl 4-amino(hydroxyimino)methyl-2-fluorobenzoate

[Chemical Formula 4]

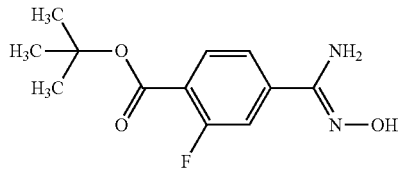

A 50% aqueous solution of hydroxylamine (60 mL, 100 mmol) was added to an ethanol (100 mL)-tetrahydrofuran (50 mL) solution of the compound obtained in Reference Example 1 (11.0 g, 66.6 mmol), and the mixture was stirred at 80° C. for 2 hours. The reaction mixture was cooled to room temperature, and then the solvent was distilled off under reduced pressure. The resulting residue was washed with water, and was dried at 40° C. for 2 days under reduced pressure. Thus, the title compound (150.0 g, yield: 98%) was obtained.

$^1$H-NMR (400 MHz, CDCl$_3$) δ ppm:

7.89 (1H, t, J=8 Hz), 7.44 (2H, dd, J=8, 2 Hz), 7.39 (2H, dd, J=11, 2 Hz), 4.90 (2H, s), 1.60 (9H, s).

Reference Example 3

Cyclopropyl(4-hydroxyphenyl)methanone

[Chemical Formula 5]

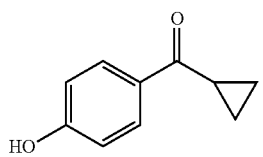

4-chloropropyl(4-hydroxyphenyl)methanone (25.1 g, 127 mmol) was added to a 2 N aqueous solution of sodium hydroxide (283 mL, 566 mmol) in several portions under ice cooling. The reaction mixture was allowed to warm up to room temperature, and was stirred for 6 hours, and then dilute sulfuric acid (1.8 N) was added to the reaction mixture under ice cooling until a pH value of 2 was obtained. The reaction mixture was subjected to extraction twice with ethyl acetate. The organic layer thus obtained was washed with water and brine, and then was dried over anhydrous magnesium sulfate. The solvent was distilled off under reduced pressure, and the resulting residue was purified by silica gel column chromatography (hexane:ethyl acetate=4:1→2:1, v/v) to give the title compound (17.7 g, yield: 86%).

$^1$H-NMR (400 MHz, CDCl$_3$) δ ppm:

7.99-7.96 (2H, m), 6.93-6.89 (2H, m), 6.16 (1H, s), 2.67-2.61 (1H, m), 1.28-1.18 (2H, m), 1.09-0.97 (2H, m).

Reference Example 4

(2S)-2-Acetoxy butyric acid

[Chemical Formula 6]

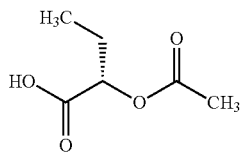

Sodium acetate (11.9 g, 146 mmol) and tert-butyl nitrite (15.0 g, 146 mmol) were added to an acetic acid (300 mL) solution of (2S)-2-aminobutyric acid (10.0 g, 97.0 mmol) under ice cooling, and was stirred at 60° C. for 2 hours. The reaction mixture was cooled to room temperature, and then the solvent was distilled off under reduced pressure. Water was added to the residue, and the mixture was subjected to extraction twice with ethyl acetate. The organic layer thus obtained was washed with water and brine, and then was dried over anhydrous sodium sulfate. The solvent was distilled off under reduced pressure, further the residue was azeotropically boiled with 1,4-dioxane (50 mL) twice. Thus, the title compound (8.4 g, yield: 60%) was obtained.

$^1$H-NMR (400 MHz, CDCl$_3$) δ ppm:

5.00 (1H, m), 2.15 (3H, s), 1.94-1.90 (2H, m), 1.03 (3H, t, J=7 Hz);

MS (FAB$^+$) m/z: 147 [M+H]$^+$.

Reference Example 5 tert-Butyl 4-{5-[(1S)-1-acetoxypropyl]-1,2,4-oxadiazol-3-yl}-2-fluorobenzoate

[Chemical Formula 7]

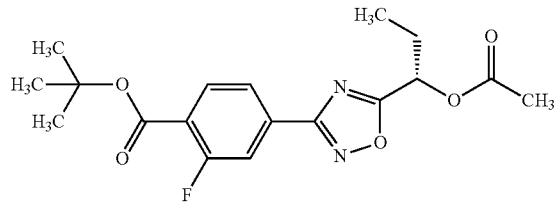

1-Hydroxybenzotriazole monohydrate (7.2 g, 53.0 mmol) and N-(3-dimethylaminopropyl)-N'-ethylcarbodiimide (20.3 g, 159 mmol) were added to an N,N-dimethylformamide (200 mL) solution of the compound obtained in Reference Example 4 (7.8 g, 53.0 mmol) at room temperature, and the mixture was stirred at the same temperature for 30 minutes. The compound obtained in Reference Example 2 (13.5 g, 53.0 mmol) was added, and the mixture was stirred for 30 minutes, and further stirred at 100° C. for 3 hours. After the reaction mixture was cooled to room temperature, water was added to the reaction mixture, and the mixture was subjected to extraction twice with ethyl acetate. The organic layer thus obtained was washed with water and a 10% aqueous solution of sodium chloride, and then was dried over anhydrous sodium sulfate. The solvent was distilled off under reduced pressure, and the resulting residue was purified by silica gel column chromatography (hexane:ethyl acetate=95:5→85:15, v/v) to give the title compound (14.7 g, yield: 76%).

$^1$H-NMR (400 MHz, CDCl$_3$) δ ppm:

7.96 (1H, t, J=8 Hz), 7.90 (1H, dd, J=8, 2 Hz), 7.84 (1H, dd, J=11, 2 Hz), 5.92 (1H, t, J=7 Hz), 2.21 (3H, s), 2.16-2.08 (2H, m), 1.62 (9H, s), 1.05 (3H, t, J=7 Hz);

MS (FAB$^+$) m/z: 365 [M+H]$^+$.

Reference Example 6 tert-Butyl 2-fluoro-4-{5-[(1S)-1-hydroxypropyl]-1,2,4-oxadiazol-3-yl}benzoate

[Chemical Formula 8]

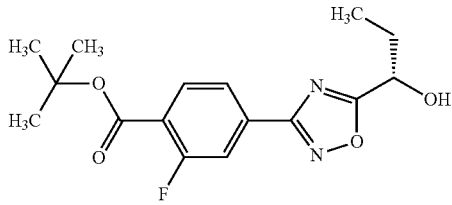

Potassium carbonate (8.4 g, 61 mmol) was added to a methanol (100 mL) solution of the compound obtained in Reference Example 5 (14.7 g, 40.3 mmol) under ice cooling, and the mixture was stirred at the same temperature for 30 minutes. 2 N Hydrochloric acid was added to the reaction mixture at the same temperature until a pH value of 6.0 was obtained. The reaction mixture was subjected to extraction twice with ethyl acetate, and the organic layer thus obtained was washed with water and brine, and then was dried over anhydrous sodium sulfate. The solvent was distilled off under reduced pressure, and the resulting residue was purified by silica gel column chromatography (hexane:ethyl acetate=95:5→80:20, v/v) to give the title compound (12.9 g, yield: 84%).

$^1$H-NMR (400 MHz, CDCl$_3$) δ ppm:
7.97 (1H, t, J=8 Hz), 7.91 (1H, d, J=8 Hz), 7.85 (1H, d, J=11 Hz), 4.98 (1H, q, J=6 Hz), 2.54 (1H, brs), 2.14-1.96 (2H, m), 1.62 (9H, s), 1.08 (3H, t, J=7 Hz);
MS (FAB$^+$) m/z: 323 [M+H]$^+$.

Reference Example 7 tert-Butyl 4-(5-{(1R)-1-[4-(cyclopropylcarbonyl)phenoxy]propyl}-1,2,4-oxadiazol-3-yl)-2-fluorobenzoate

[Chemical Formula 9]

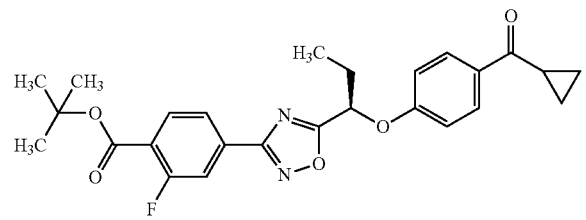

di-Tert-butyl azodicarboxylate (260 mg, 1.11 mmol) and triphenylphosphine (300 mg, 1.11 mmol) were added to a tetrahydrofuran solution (10 mL) of the compound obtained in Reference Example 6 (300 mg, 0.931 mmol) and the compound obtained in Reference Example 3 (150 mg, 0.925 mmol) at room temperature, and the mixture was stirred at the same temperature for one hour. The solvent was distilled off under reduced pressure, and the resulting residue was purified by silica gel column chromatography (hexane:ethyl acetate=95:5→80:20, v/v) to give the title compound (236 mg, yield: 55%).

$^1$H-NMR (400 MHz, CDCl$_3$) δ ppm:
8.00-7.94 (3H, m), 7.90-7.87 (1H, m), 7.84-7.81 (1H, m), 7.06-7.04 (2H, m), 5.52 (1H, dd, J=7, 6 Hz), 2.63-2.57 (1H, m), 2.34-2.25 (2H, m), 1.61 (9H, s), 1.21-1.18 (2H, m), 1.14 (3H, t, J=7 Hz), 1.01-0.98 (2H, m);
MS (FAB$^+$) m/z: 466 [M+H]$^+$.

Reference Example 8

4-(5-{(1R)-1-[4-(Cyclopropylcarbonyl)phenoxy]propyl}-1,2,4-oxadiazol-3-yl)-2-fluorobenzoic acid

[Chemical Formula 10]

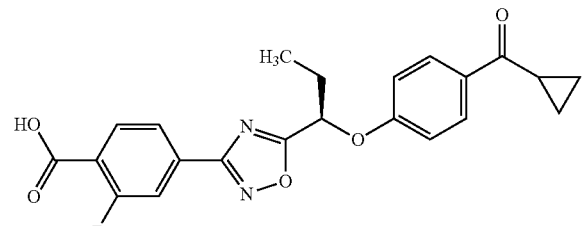

Trifluoroacetic acid (10 mL) was added to a dichloromethane (1 mL) solution of the compound obtained in Reference Example 7 (236 mg, 0.506 mmol) at room temperature, and the mixture was stirred for 40 minutes. The solvent was distilled off under reduced pressure, and the resulting residue was washed with isopropyl ether. Thus, the title compound (195 mg, yield: 94%) was obtained.

$^1$H-NMR (400 MHz, CDCl$_3$) δ ppm:
8.14 (1H, t, J=8 Hz), 8.01-7.89 (4H, m), 7.04 (2H, dd, J=7, 2 Hz), 5.54 (1H, dd, J=7, 6 Hz), 2.63-2.57 (1H, m), 2.35-2.21 (2H, m), 1.22-1.18 (2H, m), 1.15 (3H, q, J=5 Hz), 1.02-0.99 (2H, m);
MS (FAB$^+$) m/z: 411 [M+H]$^+$.

Reference Example 9 tert-Butyl 2-fluoro-4-{5-[(1S)-1-hydroxyethyl]-1,2,4-oxadiazol-3-yl}benzoate

[Chemical Formula 11]

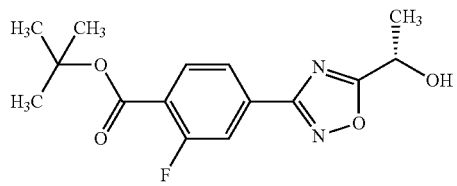

1-Hydroxybenzotriazole monohydrate (16.7 g, 109 mmol) and N-(3-dimethylaminopropyl)-N'-ethylcarbodiimide (41.8 g, 218 mmol) were added to a dimethylformamide (540 mL) solution of (2S)-2-acetoxy propionic acid (14.4 g, 109 mmol) at room temperature, and the mixture was stirred at the same temperature for 30 minutes. The compound obtained in Reference Example 2 (27.7 g, 109 mmol) was added, and the mixture was stirred for 10 minutes, and further stirred at 90° C. for 3 hours. After the reaction mixture was cooled to room temperature, water and a 10% aqueous solution of sodium chloride were added to the reaction mixture, and the mixture was subjected to extraction twice with ethyl acetate. The organic layer thus obtained was washed with a 10% aqueous solution of sodium chloride and a saturated aqueous solution of sodium hydrogen carbonate, and then was dried over anhydrous sodium sulfate. The solvent was distilled off under reduced pressure, and the resulting residue was purified by silica gel column chromatography (hexane:ethyl acetate=95:5→85:15, v/v).

Potassium carbonate (12.7 g, 91.6 mmol) was added to a methanol (360 mL) solution of the obtained tert-butyl 4-{5-[(1S)-1-acetoxyethyl]-1,2,4-oxadiazol-3-yl}-2-fluorobenzoate (32.1 g, 91.6 mmol) under ice cooling, and the mixture was stirred at the same temperature for 30 minutes. 2 N Hydrochloric acid was added to the reaction mixture at the same temperature until a pH value of 6.0 was obtained, and the solvent was distilled off under reduced pressure. Water was added to the resulting residue, and the mixture was subjected to extraction twice with ethyl acetate. The organic layer thus obtained was dried over anhydrous sodium sulfate. The solvent was distilled off under reduced pressure, and the resulting residue was solidified by using hexane. Thus, the title compound (26.4 g, yield: 93%) was obtained.

$^1$H-NMR (400 MHz, CDCl$_3$) δ ppm:
7.97 (1H, t, J=8 Hz), 7.90 (1H, d, J=8 Hz), 7.84 (1H, d, J=5 Hz), 5.18 (1H, q, J=7 Hz), 1.73 (4H, d, J=7 Hz), 1.60 (9H, s);
MS (FAB$^+$) m/z: 309 [M+H]$^+$.

Reference Example 10 tert-Butyl 4-(5-{(1R)-1-[4-(cyclopropylcarbonyl)phenoxy]ethyl}-1,2,4-oxadiazol-3-yl)-2-fluorobenzoate

[Chemical Formula 12]

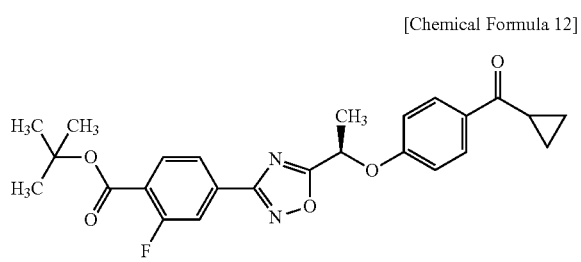 [SMILES: C[C@@H](Oc1ccc(C(=O)C2CC2)cc1)c1nc(-c2ccc(C(=O)OC(C)(C)C)c(F)c2)no1]

Triphenylphosphine (5.62 mg, 21.4 mmol) and di-tert-butyl azodicarboxylate (4.93 g, 21.4 mmol) were added to a tetrahydrofuran solution (190 mL) of the compound obtained in Reference Example 9 (6.00 g, 19.5 mmol) and the compound obtained in Reference Example 3 (3.47 g, 21.4 mmol) at room temperature, and the mixture was stirred at the same temperature for 40 minutes. The solvent was distilled off under reduced pressure, and the resulting residue was purified by silica gel column chromatography (hexane:ethyl acetate=95:5→75:25, v/v) to give the title compound (7.65 g, yield: 87%).

$^1$H-NMR (400 MHz, CDCl$_3$) δ ppm:
8.02-7.94 (3H, m), 7.89 (1H, d, J=8 Hz), 7.83 (1H, d, J=8 Hz), 7.05 (2H, d, J=8 Hz), 5.75 (1H, q, J=7 Hz), 2.63-2.59 (1H, m), 1.92 (3H, d, J=4 Hz), 1.48 (9H, s), 1.20 (2H, m), 1.01-0.99 (2H, m).

Reference Example 11

4-(5-{(1R)-1-[4-(Cyclopropylcarbonyl)phenoxy]ethyl}-1,2,4-oxadiazol-3-yl)-2-fluorobenzoic acid

[Chemical Formula 13]

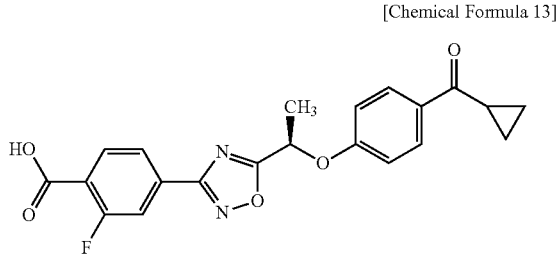 [SMILES: C[C@@H](Oc1ccc(C(=O)C2CC2)cc1)c1nc(-c2ccc(C(=O)O)c(F)c2)no1]

A dichloromethane (20 mL) solution of trifluoroacetic acid (20 mL) was added to a dichloromethane (40 mL) solution of the compound obtained in Reference Example 10 (7.65 g, 16.9 mmol) at room temperature, and the mixture was stirred for one hour. The solvent was distilled off under reduced pressure, and the resulting residue was solidified by using hexane:ethyl acetate (4:1, v/v). Thus, the title compound (4.90 g, yield: 73%) was obtained.

$^1$H-NMR (400 MHz, CDCl$_3$) δ ppm:
8.14 (1H, t, J=8 Hz), 8.01 (2H, d, J=9 Hz), 7.98-7.96 (1H, m), 7.93-7.90 (1H, m), 7.06 (2H, d, J=9 Hz), 5.76 (1H, q, J=7 Hz), 2.64-2.57 (1H, m), 1.92 (3H, d, J=7 Hz), 1.23-1.18 (2H, m), 1.03-0.98 (2H, m);
MS (FAB$^+$) m/z: 397 [M+H]$^+$.

Reference Example 12

1-[4-(Benzyloxy)phenyl]=2,2-dimethylpropane-1-one

[Chemical Formula 14]

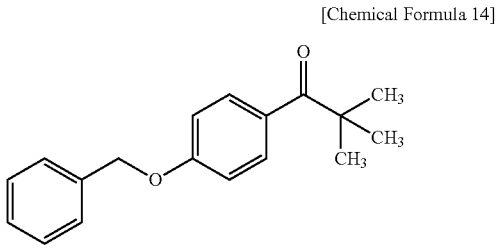 [SMILES: CC(C)(C)C(=O)c1ccc(OCc2ccccc2)cc1]

Magnesium (305 mg, 1.54 mmol) was added to a tetrahydrofuran solution (50 mL) of 4-benzyloxybromobenzene (3.00 g, 11.4 mmol) at room temperature, and the mixture was stirred at 60° C. for 30 minutes. The reaction mixture was cooled to 0° C., 1 M tetrahydrofuran solution (12 mL, 12 mmol) of pivalonitrile was added, and the mixture was stirred at room temperature for 2 hours. Subsequently, water was added to the reaction mixture, and the mixture was subjected to extraction once with ethyl acetate. The organic layer thus obtained was washed with water and brine, and then was dried over anhydrous sodium sulfate. The solvent was distilled off under reduced pressure, and the resulting residue was purified by silica gel column chromatography (hexane:ethyl acetate=99:1→90:10, v/v) to give the title compound (900 mg, yield: 29%).

$^1$H-NMR (400 MHz, CDCl$_3$) δ ppm:
7.86-7.83 (2H, m), 7.34-7.44 (5H, m), 6.96-6.98 (2H, m), 5.12 (2H, s), 1.37 (9H, s).

Reference Example 13

1-(4-Hydroxymethyl)-2,2-dimethylpropane-1-one

[Chemical Formula 15]

10% palladium on carbon (90 mg) was added to a methanol (30 mL) solution of the compound obtained in Reference Example 12 (900 mg, 3.35 mmol), and the mixture was stirred at room temperature for 2 hours in a hydrogen atmosphere. Subsequently, the reaction mixture was filtered through Celite, and the solvent was distilled off under reduced pressure from the mother liquor. The resulting residue was purified by silica gel column chromatography (hexane:ethyl acetate=80:20→50:50, v/v) to give the title compound (550 mg, yield: 92%).

$^1$H-NMR (400 MHz, CDCl$_3$) δ ppm:
7.82-7.80 (2H, m), 6.86-6.84 (2H, m), 5.77-5.61 (1H, brs), 1.37 (9H, s).

Reference Example 14 tert-Butyl 4-(5-{(1R)-1-[4-(2,2-dimethylpropanoyl)phenoxy]propyl}-1,2,4-oxadiazol-3-yl)-2-fluorobenzoate

[Chemical Formula 16]

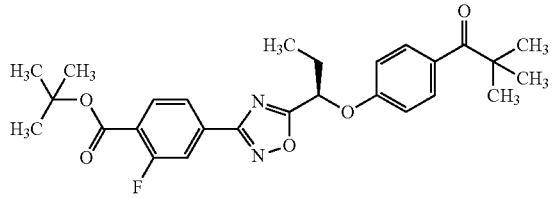

di-Tert-butyl azodicarboxylate (852 mg, 3.70 mmol) and triphenylphosphine (971 mg, 3.70 mmol) were added to a tetrahydrofuran solution (30 mL) of the compound obtained in Reference Example 6 (993 mg, 3.08 mmol) and the compound obtained in Reference Example 13 (550 mg, 3.08 mmol) at room temperature, and the mixture was stirred at the same temperature for one hour. The solvent was distilled off under reduced pressure, and the resulting residue was purified by silica gel column chromatography (hexane:ethyl acetate=95:5→80:20, v/v) to give a crude product containing the title compound (1.29 g).

Reference Example 15

4-(5-{(1R)-1-[4-(2,2-Dimethylpropanoyl)phenoxy]propyl}-1,2,4-oxadiazol-3-yl)-2-fluorobenzoic acid

[Chemical Formula 17]

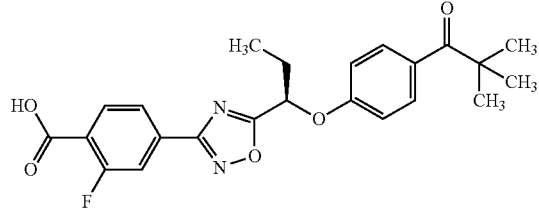

Trifluoroacetic acid (10 mL) was added to a dichloromethane (10 mL) solution of the compound obtained in Reference Example 14 (1.29 g) at room temperature, and the mixture was stirred for one hour. The solvent was distilled off under reduced pressure, and the resulting residue was washed with isopropyl ether. Thus, a crude product containing the title compound (900 mg) was obtained.

Reference Example 16

Cyclobutyl(4-hydroxyphenyl)methanone

[Chemical Formula 18]

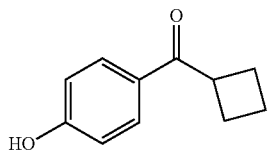

Aluminum chloride (1.59 g, 11.9 mmol) was added to a dichloromethane (10 mL) solution of phenol (1.03 g, 10.9 mmol) at room temperature, and the mixture was stirred at the same temperature for 45 minutes. Cyclobutanecarboxylic acid chloride (1.33 mL, 11.7 mmol) was added dropwise to the obtained reaction mixture at room temperature, and the mixture was stirred at the same temperature for 4 hours. Further, aluminum chloride (1.58 g, 11.8 mmol) was added at room temperature, and the mixture was stirred. The aluminum chloride was confirmed to be dissolved thoroughly, and then the mixture was stood still overnight. The reaction mixture was added to hydrochloric acid under ice cooling, and the mixture was subjected to extraction once with ethyl acetate. The organic layer thus obtained was washed with brine twice, and then was dried over anhydrous magnesium sulfate. The solvent was distilled off under reduced pressure, and the resulting residue was purified by silica gel column chromatography (hexane:ethyl acetate=90:10->80:20, v/v) to give the title compound (993 mg, yield: 51%).

$^1$H-NMR (400 MHz, CDCl$_3$) δ ppm:

7.84 (2H, dt, J=9, 2 Hz), 6.87 (2H, dt, J=9, 2 Hz), 5.64 (1H, brs), 4.00-3.91 (1H, m), 2.44-2.39 (2H, m), 2.30-2.26 (2H, m), 2.13-2.02 (1H, m), 1.95-1.85 (1H, m).

Reference Example 17

4-(5-{(1R)-1-[4-(Cyclobutylcarbonyl)phenoxy]propyl}-1,2,4-oxadiazol-3-yl)-2-fluorobenzoic acid

[Chemical Formula 19]

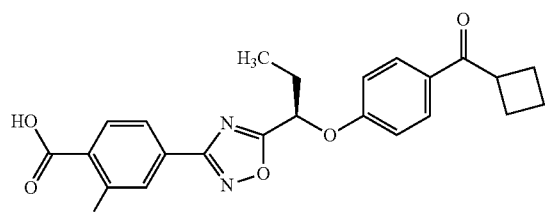

Triphenylphosphine (670 mg, 2.55 mmol) and di-tert-butyl azodicarboxylate (588 mg, 2.55 mmol) were added to a tetrahydrofuran solution (23 mL) of the compound obtained in Reference Example 6 (716 mg, 2.32 mmol) and the compound obtained in Reference Example 16 (409 mg, 2.32 mmol) at room temperature, and the mixture was stirred at the same temperature for 40 minutes. The solvent was distilled off under reduced pressure, and the resulting residue was purified by silica gel column chromatography (hexane→hexane:ethyl acetate=90:10, v/v).

Trifluoroacetic acid (5 mL) was added to a dichloromethane (5 mL) solution of the obtained tert-butyl 4-(5-{(1R)-1-[4-(cyclobutylcarbonyl)phenoxy]propyl}-1,2,4-oxadiazol-3-yl)-2-fluorobenzoate at room temperature, and the mixture was stirred for one hour. The solvent was distilled off under reduced pressure, and the resulting residue was solidified by using hexane:ethyl acetate (5:1, v/v). Thus, the title compound (531 mg, yield: 56%) was obtained.

$^1$H-NMR (400 MHz, CDCl$_3$) δ ppm:

8.14 (1H, t, J=8 Hz), 7.97 (1H, d, J=8 Hz), 7.91 (1H, d, J=11 Hz), 7.87 (2H, d, J=9 Hz), 7.01 (2H, d, J=9 Hz), 5.51 (1H, t, J=6 Hz), 3.93 (1H, m), 2.45-2.20 (6H, m), 2.12-2.01 (1H, m), 1.95-1.85 (1H, m), 1.14 (3H, t, J=7 Hz);

MS (FAB") m/z: 425 [M+H]$^+$.

Reference Example 18

4-Chloro-2-fluoro-1-(4-fluorophenyl)butan-1-one

[Chemical Formula 20]

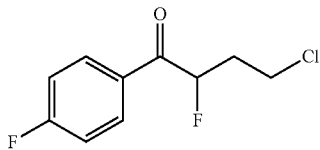

A 1,4-dioxane (50 mL) solution of bromine (8.76 g, 54.8 mmol) was added to a 1,4-dioxane (50 mL) solution of 4-chloro-4'-fluorobutyrophenone (10.0 g, 49.8 mmol) at room temperature over 15 minutes, and the mixture was stirred at the same temperature for 10 minutes. Water was added to the reaction mixture, and the mixture was subjected to extraction twice with hexane. The organic layer thus obtained was washed with water, a saturated aqueous solution of sodium hydrogen carbonate, an aqueous solution of 1.5 M sodium sulfite, and brine, and then was dried over anhydrous sodium sulfate. A portion (13.0 g) of a crude product (14.3 g) obtained by distilling off the solvent under reduced pressure was dissolved in N,N-dimethylformamide (90 mL), and 18-crown-6 (18.4 g, 69.8 mmol) and potassium fluoride (4.05 g, 69.8 mmol) were added to the mixture at room temperature. The mixture was stirred at the same temperature for 2 and a half hours, and then 18-crown-6 (6.15 g, 23.3 mmol) and potassium fluoride (1.35 g, 23.3 mmol) were added to the mixture, and the mixture was further stirred at the same temperature for one hour. Water was added to the reaction mixture, and the mixture was subjected to extraction twice with hexane. The organic layer thus obtained was washed with water and brine, and then was dried over anhydrous sodium sulfate. The solvent was distilled off under reduced pressure, and the resulting residue was purified by silica gel column chromatography (hexane:ethyl acetate=100:0→95:5, v/v) to give the title compound (5.47 g, yield: 55%).

$^1$H-NMR (500 MHz, CDCl$_3$) δ ppm:
8.04 (2H, dd, J=9, 5 Hz), 7.18 (2H, dd, J=9, 8 Hz), 5.84 (1H, ddd, J=49, 8, 4 Hz), 3.84-3.74 (2H, m), 2.46-2.35 (2H, m).

Reference Example 19

(1-Fluorocyclopropyl)(4-fluorophenyl)methanone

[Chemical Formula 21]

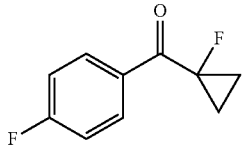

A tetrahydrofuran solution (3.97 mL, 4.33 mmol) of 1.09 M sodium bis(trimethylsilyl)amide was added to a THF (8.0 mL) solution of the compound obtained in Reference Example 18 (861 mg, 3.94 mmol) at 0° C. over 30 minutes, and the mixture was stirred at room temperature for 2.5 hours. A saturated aqueous solution of ammonium chloride and water were added to the reaction mixture, and the mixture was subjected to extraction twice with hexane. The organic layer thus obtained was washed with water and brine, and then was dried over anhydrous sodium sulfate. The solvent was distilled off under reduced pressure, and the resulting residue was purified by silica gel column chromatography (hexane:ethyl acetate=95:5, v/v) to give the title compound (336 mg, yield: 47%).

$^1$H-NMR (500 MHz, CDCl$_3$) δ ppm:
8.10-8.05 (2H, m), 7.15 (2H, t, J=9 Hz), 1.61-1.54 (2H, m), 1.52-1.45 (2H, m).

Reference Example 20

(1-Fluorocyclopropyl){4-[(4-methoxybenzyl)oxy]phenyl}methanone

[Chemical Formula 22]

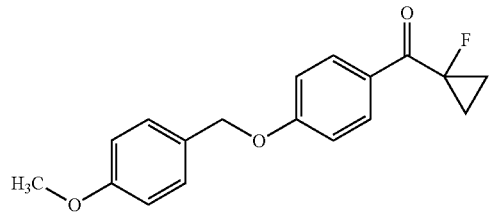

Potassium tert-butoxide (225 mg, 2.00 mmol) was added to an N,N-dimethylformamide (9.0 mL) solution of the compound obtained in Reference Example 19 (332 mg, 1.82 mmol) and 4-methoxybenzyl alcohol (250 μL, 2.00 mmol) at room temperature, and the mixture was stirred at room temperature for 1.5 hours. A saturated aqueous solution of ammonium chloride and water were added to the reaction mixture, and the mixture was stirred at room temperature for one hour, and then the precipitated solid was filtered and washed with a water and 2-propanol-water (1:1) liquid mixture. Thus, the title compound (396 mg, yield: 72%) was obtained.

$^1$H-NMR (500 MHz, CDCl$_3$) δ ppm:
8.05 (2H, dd, J=9, 1 Hz), 7.36 (2H, d, J=9 Hz), 7.02 (2H, d, J=9 Hz), 6.93 (2H, d, J=9 Hz), 5.07 (2H, s), 3.82 (3H, s), 1.58-1.51 (2H, m), 1.48-1.40 (2H, m).

Reference Example 21

(1-Fluorocyclopropyl)(4-hydroxyphenyl)methanone

[Chemical Formula 23]

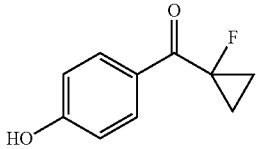

Methanol (0.4 mL) and concentrated hydrochloric acid (0.4 mL) were added to a 1,4-dioxane (4.0 mL) solution of the compound obtained in Reference Example 20 (392 mg, 1.30 mmol) at room temperature, and the mixture was stirred at the same temperature for 2 hours, and then was heated to 60° C. and further stirred for 7 hours. The reaction mixture was cooled to room temperature. Water was added to the reaction mixture, and the mixture was subjected to extraction twice with ethyl acetate. The organic layer thus obtained was washed with brine, and then was dried over anhydrous sodium sulfate. The solvent was distilled off under reduced pressure, and the resulting residue was purified by silica gel column chromatography (hexane:ethyl acetate=90:10→75:25, v/v) to give the title compound (217 mg, yield: 92%).

¹H-NMR (500 MHz, CDCl₃) δ ppm:
8.03 (2H, dd, J=9, 1 Hz), 6.89 (2H, d, J=9 Hz), 5.30 (1H, s), 1.58-1.51 (2H, m), 1.49-1.40 (2H, m).

Reference Example 22 tert-Butyl 2-fluoro-4-{5-[(1R)-1-{4-[(1-fluorocyclopropyl)carbonyl]phenoxy}propyl]-1,2,4-oxadiazol-3-yl}benzoate

[Chemical Formula 24]

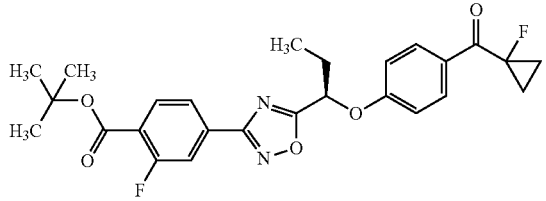

Triphenylphosphine (293 mg, 1.12 mmol) and di-tert-butyl azodicarboxylate (253 mg, 1.12 mmol) were added to a tetrahydrofuran (5.0 mL) solution of the compound obtained in Reference Example 6 (360 mg, 1.12 mmol) and the compound obtained in Reference Example 21 (183 mg, 1.02 mmol) at 0° C., and the mixture was stirred at the same temperature for 5 minutes, and then further stirred at room temperature for one hour. The solvent was distilled off under reduced pressure, and the resulting residue was purified by silica gel column chromatography (hexane:ethyl acetate=100:0→85:15, v/v) to give the title compound (396 mg, yield: 80%).

¹H-NMR (500 MHz, CDCl₃) δ ppm:
8.04 (2H, dd, J=9, 1 Hz), 7.97 (1H, dd, J=8, 7 Hz), 7.89 (1H, dd, J=8, 1 Hz), 7.83 (1H, dd, J=11, 1 Hz), 7.04 (2H, d, J=9 Hz), 5.53 (1H, dd, J=7, 6 Hz), 2.34-2.21 (2H, m), 1.61 (9H, s), 1.55-1.51 (2H, m), 1.48-1.40 (2H, m), 1.14 (3H, t, J=7 Hz).

Reference Example 23

2-Fluoro-4-{5-[(1R)-1-{4-[(1-fluorocyclopropyl)carbonyl]phenoxy}propyl]-1,2,4-oxadiazol-3-yl}benzoic acid

[Chemical Formula 25]

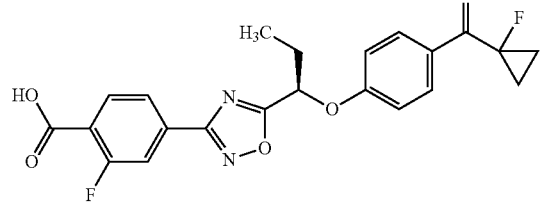

Trifluoroacetic acid (2.0 mL) was added to a dichloromethane (2.0 mL) solution of the compound obtained in Reference Example 22 (390 mg, 0.805 mmol) at room temperature, and the mixture was stirred at the same temperature for one hour. The solvent was distilled off under reduced pressure, and the resulting residue was washed with a hexane-ethyl acetate liquid mixture. Thus, the title compound (283 mg, yield: 82%) was obtained.

¹H-NMR (500 MHz, CDCl₃) δ ppm:
8.14 (1H, dd, J=8, 7 Hz), 8.04 (2H, dd, J=9, 1 Hz), 7.97 (1H, dd, J=8, 1 Hz), 7.91 (1H, dd, J=11, 1 Hz), 7.04 (2H, d, J=9 Hz), 5.54 (1H, dd, J=7, 6 Hz), 2.36-2.20 (2H, m), 1.57-1.51 (2H, m), 1.48-1.40 (2H, m), 1.15 (3H, t, J=7 Hz).

Reference Example 24 tert-Butyl 2-fluoro-4-{5-[(1R)-1-(4-isobutyrylphenoxy)propyl]-1,2,4-oxadiazol-3-yl}benzoate

[Chemical Formula 26]

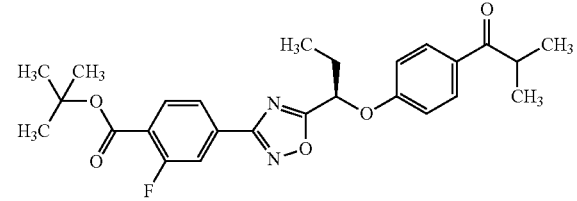

Triphenylphosphine (297 mg, 1.13 mmol) and di-tert-butyl azodicarboxylate (261 mg, 1.13 mmol) were added to a tetrahydrofuran (5.0 mL) solution of the compound obtained in Reference Example 6 (332 mg, 1.03 mmol) and 4'-hydroxy-2-methylpropiophenone (186 mg, 1.13 mmol) at 0° C., and the mixture was stirred at the same temperature for 5 minutes, and then further stirred at room temperature for one hour. The solvent was distilled off under reduced pressure, and the resulting residue was purified by silica gel column chromatography (hexane:ethyl acetate=95:5→85:15, v/v) to give the title compound (268 mg, yield: 56%).

¹H-NMR (500 MHz, CDCl₃) δ ppm:
7.98-7.94 (1H, m), 7.93 (2H, d, J=9 Hz), 7.89 (1H, dd, J=8, 2 Hz), 7.83 (1H, d, J=9 Hz), 7.03 (2H, dd, J=7, 2 Hz), 5.51 (1H, dd, J=7, 6 Hz), 3.54-3.42 (1H, m), 2.34-2.18 (2H, m), 1.55 (9H, s), 1.18 (6H, dd, J=7, 2 Hz), 1.14 (3H, t, J=7 Hz).

Reference Example 25

2-Fluoro-4-{5-[(1R)-1-(4-isobutyrylphenoxy)propyl]-1,2,4-oxadiazol-3-yl}benzoic acid

[Chemical Formula 27]

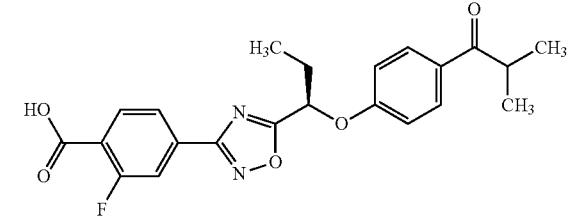

Trifluoroacetic acid (1.5 mL) was added to a dichloromethane (1.5 mL) solution of the compound obtained in Reference Example 24 (268 mg, 0.572 mmol) at room temperature, and the mixture was stirred at the same temperature for 2 hours. The solvent was distilled off under reduced pressure, and the resulting residue was washed with a hexane-ethyl acetate liquid mixture. Thus, the title compound (223 mg, yield: 94%) was obtained.

¹H-NMR (500 MHz, CDCl₃) δ ppm:
8.13 (1H, dd, J=8, 7 Hz), 7.96 (1H, dd, J=8, 2 Hz), 7.93 (2H, d, J=9 Hz), 7.91 (1H, dd, J=11, 2 Hz), 7.03 (2H, d, J=9 Hz), 5.52 (1H, dd, J=7, 6 Hz), 3.54-3.43 (1H, m), 2.35-2.19 (2H, m), 1.19 (6H, dd, J=7, 2 Hz), 1.14 (3H, t, J=7 Hz).

Reference Example 26

N-Cyclopenta-3-en-1-yl-4-(5-{(1R)-1-[4-(cyclopropylcarbonyl)phenoxy]ethyl}-1,2,4-oxadiazol-3-yl)-2-fluorobenzamide

[Chemical Formula 28]

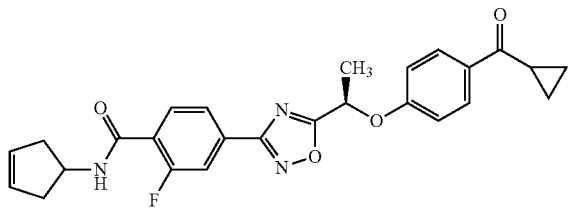

1-Hydroxybenzotriazole monohydrate (104 mg, 681 mmol) and N-(3-dimethylaminopropyl)-N'-ethylcarbodiimide (261 mg, 1.36 mmol) were added to an N,N-dimethylformamide (3 mL) solution of the compound obtained in Reference Example 11 (270 mg, 681 mmol) at room temperature, and the mixture was stirred at the same temperature for 30 minutes. Subsequently, 1-amino-3-cyclopentene hydrochloride (122 mg, 1.02 mmol) and triethylamine (142 mL, 1.02 mmol) were added, and the mixture was further stirred at the same temperature for 30 minutes. Water and a 10% aqueous solution of sodium chloride were added to the reaction mixture, and the mixture was subjected to extraction twice with ethyl acetate. The organic layer thus obtained was washed with water and a saturated aqueous solution of sodium hydrogen carbonate, and then was dried over anhydrous sodium sulfate. The solvent was distilled off under reduced pressure, and the resulting residue was purified by silica gel column chromatography (hexane:ethyl acetate=100:0→70:30, v/v) to give the title compound (212 mg, yield: 67%).

¹H-NMR (400 MHz, CDCl₃) δ ppm:
8.21 (1H, t, J=8 Hz), 8.01-7.96 (3H, m), 7.83 (1H, dd, J=12, 1 Hz), 7.05 (2H, d, J=9 Hz), 6.94-6.87 (1H, m), 5.78-5.72 (3H, m), 4.84-4.75 (1H, m), 2.88 (2H, dd, J=15, 8 Hz), 2.58-2.53 (1H, m), 2.34 (2H, dd, J=15, 4 Hz), 1.91 (3H, d, J=7 Hz), 1.23-1.17 (2H, m), 1.03-0.97 (2H, m);
MS (FAB) m/z: 462 [M+H]⁺.

Reference Example 27

(2R,3R)-3-Amino-1,2-butanediol hydrochloride

[Chemical Formula 29]

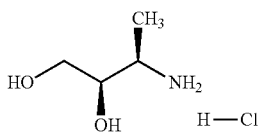

20% Palladium carbon hydroxide (108 mg) was added to an ethanol (20 mL) solution of (2R,3R,αR)-2-hydroxy-3-(N-benzyl-N-α-methylbenzylamino) butanol, Tetrahedron: Asymmetry 2002, 13, 1555-1565, (1.08 g, 3.61 mmol) at room temperature, and the mixture was stirred at 60° C. for 8 hours under hydrogen flow. The reaction mixture was cooled to room temperature, and the insoluble matter was removed by filtration through Celite. Subsequently, a portion (320 mg) of the resulting residue (466 mg) obtained by distilling off the solvent under reduced pressure was dissolved in ethanol (1.0 mL), and 4M hydrogen chloride 1,4 dioxane solution (1.13 mL, 4.54 mmol) was added at room temperature, and the mixture was stirred at the same temperature for 10 minutes. The solvent was distilled off under reduced pressure. Thus, a crude product of the title compound (354 mg) was obtained.

Example 1

4-(5-{(1R)-1-[4-(Cyclopropylcarbonyl)phenoxy]propyl}-1,2,4-oxadiazol-3-yl)-N-[(2S)-2,3-dihydroxypropyl]-2-fluorobenzamide

[Chemical Formula 30]

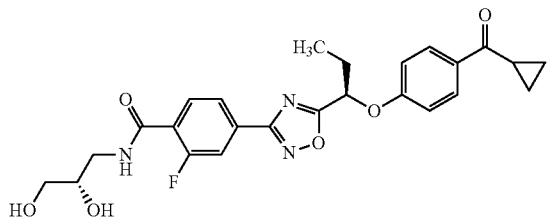

1-Hydroxybenzotriazole monohydrate (89.6 mg, 0.585 mmol) and N-(3-dimethylaminopropyl)-N'-ethylcarbodiimide (112 mg, 0.585 mmol) were added to an N,N-dimethylformamide (1.4 mL) solution of the compound obtained in Reference Example 8 (200 mg, 0.487 mmol) at room temperature, and the mixture was stirred at the same temperature for 30 minutes. Subsequently, an N,N-dimethylformamide (1.0 mL) solution of (S)-3-amino-1,2-propanediol (133 mg, 1.46 mmol) was added at 0° C., and the mixture was further stirred at the same temperature for one hour. Water was added to the reaction mixture, and the mixture was subjected to extraction twice with ethyl acetate. The organic layer thus obtained was washed with a saturated aqueous solution of sodium hydrogen carbonate and brine, and then was dried over anhydrous sodium sulfate. The solvent was distilled off under reduced pressure, and the resulting residue was purified by silica gel column chromatography (dichloromethane:methanol=100:0→90:10, v/v) to give the title compound (199 mg, yield: 85%).

¹H-NMR (500 MHz, CDCl₃) δ ppm:
8.20 (1H, t, J=8 Hz), 8.03-7.98 (3H, m), 7.87 (1H, dd, J=13, 1 Hz), 7.28-7.16 (1H, m), 7.04 (2H, d, J=9 Hz), 5.53 (1H, t, J=6 Hz), 3.97-3.88 (1H, m), 3.76-3.58 (4H, m), 2.95 (1H, d, J=5 Hz), 2.81-2.72 (1H, m), 2.63-2.55 (1H, m), 2.35-2.18 (2H, m), 1.23-1.17 (2H, m), 1.15 (3H, t, J=7 Hz), 1.03-0.96 (2H, m);
MS (ES) m/z: 484 [M+H]⁺.

Example 2

N-[(1S)-2-Amino-1-(hydroxymethyl)-2-oxoethyl]-4-(5-{(1R)-1-[4-(cyclopropylcarbonyl)phenoxy]propyl}-1,2,4-oxadiazol-3-yl)-2-fluorobenzamide

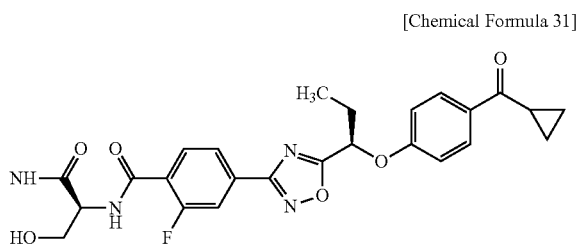 [SMILES: CC[C@@H](Oc1ccc(C(=O)C2CC2)cc1)c1nc(-c2ccc(C(=O)N[C@@H](CO)C(N)=O)c(F)c2)no1]

[Chemical Formula 31]

1-Hydroxybenzotriazole monohydrate (46.3 mg, 0.302 mmol) and N-(3-dimethylaminopropyl)-N'-ethylcarbodiimide (116 mg, 0.604 mmol) were added to a dimethylformamide (1 mL) solution of the compound obtained in Reference Example 8 (124 mg, 0.302 mmol) at room temperature, and the mixture was stirred at the same temperature for 30 minutes. L-Serinamide hydrochloride (63.7 mg, 0.453 mmol) and triethylamine (147 µL, 1.06 mmol) were added, and the mixture was stirred at the same temperature for 20 minutes. Subsequently, water and a 10% aqueous solution of sodium chloride were added to the reaction mixture, and the mixture was subjected to extraction three times with ethyl acetate. The organic layer thus obtained was washed with a saturated aqueous solution of sodium hydrogen carbonate and a 10% aqueous solution of sodium chloride, and then was dried over anhydrous sodium sulfate. The solvent was distilled off under reduced pressure, and the resulting residue was purified by silica gel column chromatography (hexane:ethyl acetate=70:30→ethyl acetate, v/v) to give the title compound (69.5 mg, yield: 67%).

$^1$H-NMR (400 MHz, CDCl$_3$) δ ppm:

8.20 (1H, t, J=8 Hz), 8.02-7.99 (3H, m), 7.92-7.89 (2H, m), 7.05 (2H, t, J=9 Hz), 6.77 (1H, s), 5.55-5.51 (2H, m), 4.72-4.68 (1H, m), 4.44-4.36 (1H, m), 3.80-3.72 (1H, m), 3.07-3.01 (1H, m), 2.60 (1H, m), 2.29 (2H, dt, J=7, 7 Hz), 1.23-1.14 (2H, m), 1.03-0.98 (2H, m);

MS (FAB+) m/z: 497 [M+H]$^+$.

Example 3

4-(5-{(1R)-1-[4-(Cyclopropylcarbonyl)phenoxy]propyl}-1,2,4-oxadiazol-3-yl)-2-fluoro-N-[(1R)-2-hydroxy-1-methylethyl]benzamide

[Chemical Formula 32]

1-Hydroxybenzotriazole monohydrate (64.5 mg, 0.421 mmol), N-(3-dimethylaminopropyl)-N'-ethylcarbodiimide (182 mg, 0.949 mmol), and (R)-2-amino-1-propanol (53.5 mg, 0.712 mmol) were added to an N,N-dimethylformamide (5 mL) solution of the compound obtained in Reference Example 8 (195 mg, 0.475 mmol) at room temperature, and the mixture was stirred at the same temperature for one hour. Subsequently, water was added to the reaction mixture, and the mixture was subjected to extraction once with ethyl acetate. The organic layer thus obtained was washed with water and a 10% aqueous solution of sodium chloride, and then was dried over anhydrous sodium sulfate. The solvent was distilled off under reduced pressure, and the resulting residue was purified by silica gel column chromatography (hexane:ethyl acetate=50:50→30:70, v/v) to give the title compound (152.9 mg, yield: 69%).

$^1$H-NMR (400 MHz, CDCl$_3$) δ ppm:

8.20 (1H, t, J=8 Hz), 8.01-7.97 (3H, m), 7.85 (1H, dd, J=12, 1 Hz), 7.06-7.03 (2H, m), 6.90 (1H, dd, J=12, 7 Hz), 5.52 (1H, t, J=6 Hz), 4.38-4.31 (1H, m), 3.81 (1H, dd, J=11, 4 Hz), 3.68 (1H, dd, J=11, 6 Hz), 2.63-2.56 (1H, m), 2.44 (1H, brs), 2.34-2.20 (2H, m), 1.32 (3H, d, J=7 Hz), 1.22-1.18 (2H, m), 1.14 (3H, t, J=7 Hz), 1.02-0.97 (2H, m);

MS (FAB$^+$) m/z: 468 [M+H]$^+$.

Example 4

4-(5-{(1R)-1-[4-(Cyclopropylcarbonyl)phenoxy]propyl}-1,2,4-oxadiazol-3-yl)-2-fluoro-N-[(1S)-2-hydroxy-1-methylethyl]benzamide

[Chemical Formula 33]

By using the compound obtained in Reference Example 8 (250 mg, 0.609 mmol), N,N-dimethylformamide (3.0 mL), 1-hydroxybenzotriazole monohydrate (112 mg, 0.731 mmol), N-(3-dimethylaminopropyl)-N'-ethylcarbodiimide (140 mg, 0.731 mmol), and (S)-2-amino-1-propanol (142 µL, 1.83 mmol), the title compound (232 mg, yield: 81%) was obtained in the same manner as in Example 1. However, purification was performed by silica gel column chromatography (hexane:ethyl acetate=70:30→0:100, v/v).

$^1$H-NMR (500 MHz, CDCl$_3$) δ ppm:

8.20 (1H, t, J=8 Hz), 8.02-7.96 (3H, m), 7.85 (1H, dd, J=12, 1 Hz), 7.04 (2H, d J=9 Hz), 6.93-6.87 (1H, m), 5.52 (1H, dd, J=7, 6 Hz), 4.39-4.31 (1H, m), 3.81 (1H, dd, J=11, 4 Hz), 3.68 (1H, dd, J=11, 6 Hz), 2.62-2.56 (1H, m), 2.47 (1H, s), 2.35-2.20 (2H, m), 1.32 (3H, d, J=7 Hz), 1.22-1.18 (2H, m), 1.14 (3H, t, J=7 Hz), 1.02-0.97 (2H, tt, J=8, 2 Hz);

MS (ES) m/z: 468 [M+H]+.

Example 5

4-(5-{(1R)-1-[4-(Cyclopropylcarbonyl)phenoxy]propyl}-1,2,4-oxadiazol-3-yl)-N-[(2R)-2,3-dihydroxypropyl]-2-fluorobenzamide

[Chemical Formula 34]

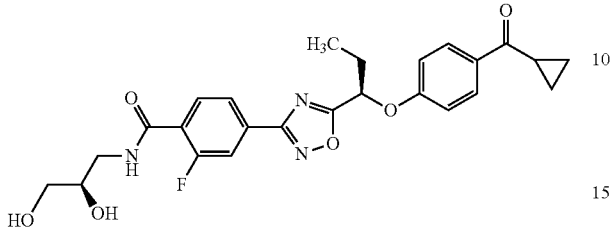

By using an N,N-dimethylformamide (1.0 mL) solution of the compound obtained in Reference Example 8 (200 mg, 0.487 mmol), N,N-dimethylformamide (1.4 mL), 1-hydroxybenzotriazole monohydrate (89.6 mg, 0.585 mmol), N-(3-dimethylaminopropyl)-N'-ethylcarbodiimide (112 mg, 0.585 mmol), and (R)-3-amino-1,2-propanediol (133 mg, 1.46 mmol), the title compound (203 mg, yield: 86%) was obtained in the same manner as in Example 1. However, purification was performed by silica gel column chromatography (dichloromethane:methanol=100:0→90:10, v/v).

$^1$H-NMR (500 MHz, CDCl$_3$) δ ppm:
8.20 (1H, t, J=8 Hz), 8.03-7.98 (3H, m), 7.87 (1H, dd, J=13, 1 Hz), 7.28-7.16 (1H, m), 7.04 (2H, d, J=9 Hz), 5.53 (1H, t, J=6 Hz), 3.97-3.88 (1H, m), 3.76-3.58 (4H, m), 2.95 (1H, d, J=5 Hz), 2.81-2.72 (1H, m), 2.63-2.55 (1H, m), 2.35-2.18 (2H, m), 1.23-1.17 (2H, m), 1.15 (3H, t, J=7 Hz), 1.03-0.96 (2H, m);
MS (ES) m/z: 484 [M+H]$^+$.

Example 6

4-(5-{(1R)-1-[4-(Cyclopropylcarbonyl)phenoxy]propyl}-1,2,4-oxadiazol-3-yl)-2-fluoro-N-[2-hydroxy-1-(hydroxymethyl)ethyl]benzamide

[Chemical Formula 35]

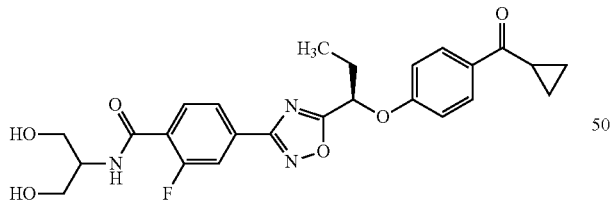

By using the compound obtained in Reference Example 8 (154 mg, 0.375 mmol), dimethylformamide (4 mL), 1-hydroxybenzotriazole monohydrate (50.7 mg, 0.331 mmol), N-(3-dimethylaminopropyl)-N'-ethylcarbodiimide (144 mg, 0.751 mmol), and 2-amino-1,3-propanediol (51.3 mg, 0.563 mmol), the title compound (110 mg, yield: 61%) was obtained in the same manner as in Example 3. However, purification was performed by silica gel column chromatography (dichloromethane:methanol=99:1→90:10, v/v).

$^1$H-NMR (400 MHz, CDCl$_3$) δ ppm:
8.19 (1H, t, J=8 Hz), 8.00-7.97 (3H, m), 7.86 (1H, dd, J=13, 2 Hz), 7.52-7.47 (1H, m), 7.04 (2H, d, J=7 Hz), 5.53 (1H, t, J=6 Hz), 4.27-4.21 (1H, m), 4.02-3.93 (4H, m), 2.62-2.56 (1H, m), 2.51 (2H, dd, J=6, 4 Hz), 2.35-2.21 (2H, m), 1.21-1.18 (2H, m), 1.15 (3H, t, J=7 Hz), 1.02-0.97 (2H, m);
MS (FAB$^+$) m/z: 484 [M+H]$^+$.

Example 7

4-(5-{(1R)-1-[4-(Cyclopropylcarbonyl)phenoxy]ethyl}-1,2,4-oxadiazol-3-yl)-2-fluoro-N-[2-hydroxy-1-(hydroxymethyl)ethyl]benzamide

[Chemical Formula 36]

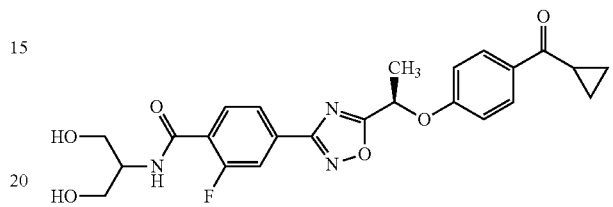

1-Hydroxybenzotriazole monohydrate (40.9 mg, 0.267 mmol) and N-(3-dimethylaminopropyl)-N'-ethylcarbodiimide (102 mg, 0.534 mmol) were added to a dimethylformamide (1.5 mL) solution of the compound obtained in Reference Example 11 (106 mg, 0.267 mmol) at room temperature, and the mixture was stirred at the same temperature for 30 minutes. 2-Amino-1,3-propanediol (36.5 mg, 0.400 mmol) was added, and the mixture was stirred at the same temperature for 20 minutes. Subsequently, water and a 10% aqueous solution of sodium chloride were added to the reaction mixture, and the mixture was subjected to extraction three times with ethyl acetate. The organic layer thus obtained was washed with a saturated aqueous solution of sodium hydrogen carbonate and a 10% aqueous solution of sodium chloride, and then was dried over anhydrous sodium sulfate. The solvent was distilled off under reduced pressure, and the resulting residue was purified by silica gel column chromatography (hexane:ethyl acetate=70:30→ethyl acetate, v/v) to give the title compound (69.5 mg, yield: 55%).

$^1$H-NMR (400 MHz, CDCl$_3$) δ ppm:
8.17 (1H, t, J=8 Hz), 7.97-7.95 (3H, m), 7.83 (1H, d, J=12 Hz), 7.47-7.44 (1H, m), 7.01 (2H, t, J=9 Hz), 5.72 (1H, q, J=7 Hz), 4.24-4.18 (1H, m), 4.00-3.94 (2H, m), 3.94-3.87 (2H, m), 2.56 (1H, dddd, J=8, 8, 5, 5 Hz), 2.37 (1H, m), 1.88 (3H, d, J=7 Hz), 1.19-1.15 (2H, m), 0.99-0.94 (2H, m);
MS (FAB$^+$) m/z: 470 [M+H]$^+$.

Example 8

4-(5-{(1R)-1-[4-(Cyclopropylcarbonyl)phenoxy]ethyl}-1,2,4-oxadiazol-3-yl)-2-fluoro-N-[(1S)-2-hydroxy-1-methylethyl]benzamide

[Chemical Formula 37]

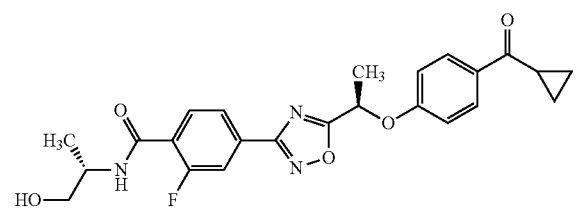

By using the compound obtained in Reference Example 11 (110 mg, 0.277 mmol), dimethylformamide (1.5 mL), 1-hydroxybenzotriazole monohydrate (42.3 mg, 0.277 mmol), N-(3-dimethylaminopropyl)-N'-ethylcarbodiimide (106 mg, 0.553 mmol), and (S)-2-amino-1-propanol (32.1 µL, 0.414 mmol), the title compound (87.8 mg, yield: 70%) was obtained in the same manner as in Example 7. However, purification was performed by silica gel column chromatography (hexane:ethyl acetate=80:20→30:70, v/v).

$^1$H-NMR (400 MHz, CDCl$_3$) δ ppm:

8.21 (1H, t, J=8 Hz), 8.03-7.99 (3H, m), 7.87 (1H, d, J=12 Hz), 7.06 (2H, d, J=8 Hz), 6.95-6.89 (1H, m), 5.77 (1H, q, J=7 Hz), 4.39-4.32 (1H, m), 3.82 (1H, dd, J=11, 4 Hz), 3.70 (1H, dd, J=11, 5 Hz), 2.62 (1H, dddd, J=8, 8, 5, Hz), 1.93 (3H, d, J=7 Hz), 1.34 (3H, d, J=7 Hz), 1.24-1.20 (2H, m), 1.04-1.00 (2H, m);

MS (FAB$^+$) m/z: 454 [M+H]$^+$.

Example 9

4-(5-{(1R)-1-[4-(Cyclopropylcarbonyl)phenoxy]ethyl}-1,2,4-oxadiazol-3-yl)-2-fluoro-N-[(1R,2R)-2-hydroxycyclopentyl]benzamide

[Chemical Formula 38]

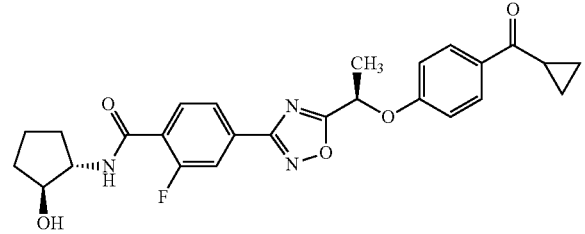

By using the compound obtained in Reference Example 11 (164 mg, 0.414 mmol), dimethylformamide (1.5 mL), 1-hydroxybenzotriazole monohydrate (63.4 mg, 0.414 mmol), N-(3-dimethylaminopropyl)-N'-ethylcarbodiimide (159 mg, 0.828 mmol), and (1R,2R)-2-aminocyclopentanol hydrochloride (85.5 mg, 0.621 mmol), the title compound (175 mg, yield: 87%) was obtained in the same manner as in Example 7. However, purification was performed by silica gel column chromatography (hexane:ethyl acetate=80:20→30:70, v/v).

$^1$H-NMR (400 MHz, CDCl$_3$) δ ppm:

8.22 (1H, t, J=8 Hz), 8.00 (3H, m), 7.86 (1H, d, J=12 Hz), 7.05 (2H, d, J=9 Hz), 6.93-6.86 (1H, m), 5.75 (1H, q, J=7 Hz), 4.19 (1H, s), 4.16-4.05 (2H, m), 2.59 (1H, dddd, J=8, 8, 4, 4 Hz), 2.32-2.23 (1H, m), 2.15-2.05 (1H, m), 1.91 (3H, d, J=7 Hz), 1.91-1.72 (1H, m), 1.62-1.52 (2H, m), 1.23-1.18 (2H, m), 1.03-0.98 (2H, m);

MS (FAB$^+$) m/z: 480 [M+H]$^+$.

Example 10

4-(5-{(1R)-1-[4-(Cyclopropylcarbonyl)phenoxy]ethyl}-1,2,4-oxadiazol-3-yl)-2-fluoro-N-[(1R)-2-hydroxy-1-methylethyl]benzamide

[Chemical Formula 39]

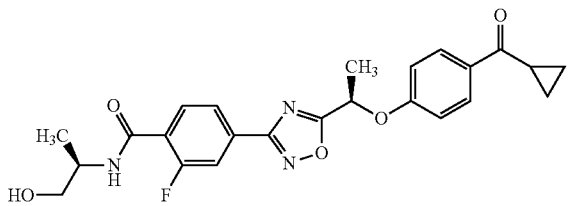

By using the compound obtained in Reference Example 11 (299 mg, 0.755 mmol), dimethylformamide (1.5 mL), 1-hydroxybenzotriazole monohydrate (115 mg, 0.755 mmol), N-(3-dimethylaminopropyl)-N'-ethylcarbodiimide (289 mg, 1.51 mmol), and (R)-2-amino-1-propanol (87.7 µL, 1.13 mmol), the title compound (262 mg, yield: 77%) was obtained in the same manner as in Example 7. However, purification was performed by silica gel column chromatography (hexane:ethyl acetate=80:20→30:70, v/v).

$^1$H-NMR (400 MHz, CDCl$_3$) δ ppm:

8.20 (1H, t, J=8 Hz), 8.02-7.97 (3H, m), 7.85 (1H, d, J=12 Hz), 7.05 (2H, d, J=12 Hz), 6.94-6.87 (1H, m), 5.75 (1H, q, J=7 Hz), 4.38-4.31 (1H, m), 3.81 (1H, dd, J=11, 4 Hz), 3.68 (1H, dd, J=11, 6 Hz), 2.60 (1H, dddd, J=8, 8, 4, 4 Hz), 1.91 (3H, d, J=7 Hz), 1.32 (3H, d, J=7 Hz), 1.22-1.18 (2H, m), 1.02-0.98 (2H, m);

MS (FAB$^+$) m/z: 454 [M+H]$^+$.

Example 11

4-(5-{(1R)-1-[4-(Cyclopropylcarbonyl)phenoxy]ethyl}-1,2,4-oxadiazol-3-yl)-2-fluoro-N-[(1S,2S)-2-hydroxycyclopentyl]benzamide

[Chemical Formula 40]

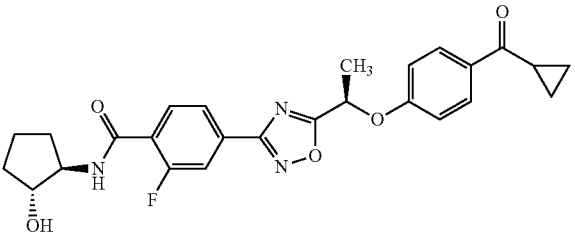

By using the compound obtained in Reference Example 11 (74.0 mg, 0.187 mmol), dimethylformamide (1 mL), 1-hydroxybenzotriazole monohydrate (28.6 mg, 0.187 mmol), N-(3-dimethylaminopropyl)-N'-ethylcarbodiimide (71.6 mg, 0.373 mmol), and (1S,2S)-2-aminocyclopentanol hydrochloride (38.5 mg, 0.280 mmol), the title compound (67.8 mg, yield: 76%) was obtained in the same manner as in Example 7. However, purification was performed by silica gel column chromatography (hexane:ethyl acetate=80:20→30:70, v/v).

¹H-NMR (400 MHz, CDCl₃) δ ppm:
8.22 (1H, t, J=8 Hz), 8.00 (3H, m), 7.86 (1H, d, J=12 Hz), 7.05 (2H, d, J=9 Hz), 6.93-6.86 (1H, m), 5.75 (1H, q, J=7 Hz), 4.19 (1H, s), 4.16-4.05 (1H, m), 2.59 (1H, dddd, J=8, 8, 4, 4 Hz), 2.32-2.23 (1H, m), 2.15-2.05 (1H, m), 1.91 (3H, d, J=7 Hz), 1.91-1.72 (1H, m), 1.62-1.52 (2H, m), 1.23-1.18 (2H, m), 1.03-0.98 (2H, m);
MS (FAB⁺) m/z: 480 [M+H]⁺.

Example 12

4-(5-{(1R)-1-[4-(2,2-Dimethylpropanoyl)phenoxy]propyl}-1,2,4-oxadiazol-3-yl)-2-fluoro-N-[2-hydroxy-1-(hydroxymethyl)ethyl]benzamide

[Chemical Formula 41]

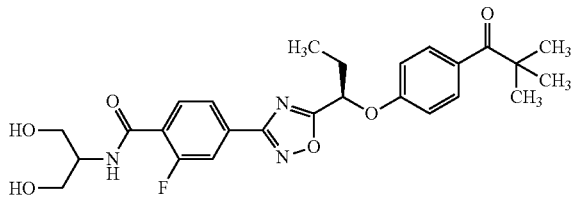

By using the compound obtained in Reference Example 15 (200 mg, 0.487 mmol), dimethylformamide (5 mL), 1-hydroxybenzotriazole monohydrate (63.4 mg, 0.414 mmol), N-(3-dimethylaminopropyl)-N'-ethylcarbodiimide (180.0 mg, 0.939 mmol), and 2-amino-1,3-propanediol (53.5 mg, 0.587 mmol), the title compound (192 mg, yield: 82%) was obtained in the same manner as in Example 3. However, purification was performed by silica gel column chromatography (hexane:ethyl acetate=50:50→30:70, v/v).
¹H-NMR (400 MHz, CDCl₃) δ ppm:
8.18 (1H, t, J=8 Hz), 7.98-7.97 (1H, m), 7.86 (1H, d, J=12 Hz), 7.81-7.77 (2H, m), 7.54-7.50 (1H, m), 7.43-7.42 (1H, m), 6.98 (2H, d, J=9 Hz), 5.48 (1H, t, J=7 Hz), 4.24 (1H, s), 4.00 (2H, dd, J=11, 4 Hz), 3.93 (2H, dd, J=11, 4 Hz), 1.34 (9H, s), 1.14 (3H, t, J=7 Hz);
MS (FAB⁺) m/z: 500 [M+H]⁺.

Example 13

4-(5-{(1R)-1-[4-(Cyclobutylcarbonyl)phenoxy]propyl}-1,2,4-oxadiazol-3-yl)-2-fluoro-N-[2-hydroxy-1-(hydroxymethyl)ethyl]benzamide

[Chemical Formula 42]

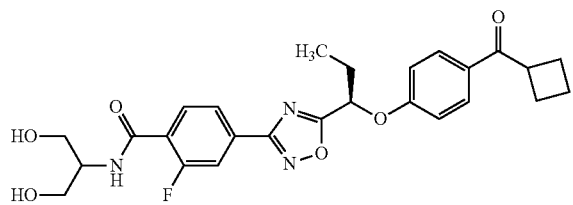

By using the compound obtained in Reference Example 17 (106 mg, 0.251 mmol), dimethylformamide (1.2 mL), 1-hydroxybenzotriazole monohydrate (38.4 mg, 0.251 mmol), N-(3-dimethylaminopropyl)-N'-ethylcarbodiimide (96.2 mg, 0.502 mmol), and 2-amino-1,3-propanediol (34.3 mg, 0.376 mmol), the title compound (92.3 mg, yield: 74%) was obtained in the same manner as in Example 7. However, purification was performed by silica gel column chromatography (hexane:ethyl acetate=70:30→ethyl acetate, v/v).
¹H-NMR (400 MHz, CDCl₃) δ ppm:
8.18 (1H, t, J=8 Hz), 7.97 (1H, d, J=8 Hz), 7.86-7.83 (3H, m), 7.52-7.46 (1H, m), 6.99 (2H, d, J=9 Hz), 5.48 (1H, t, J=6 Hz), 4.26-4.21 (1H, m), 4.01-3.87 (4H, m), 2.45-2.19 (6H, m), 2.10-2.05 (1H, m), 1.91-1.83 (1H, m), 1.12 (3H, t, J=8 Hz);
MS (FAB⁺) m/z: 498 [M+H]⁺.

Example 14

2-Fluoro-4-{5-[(1R)-1-{4-[(1-fluorocyclopropyl)carbonyl]phenoxy}propyl]-1,2,4-oxadiazol-3-yl}-N-[2-hydroxy-1-(hydroxymethyl)ethyl]benzamide

[Chemical Formula 43]

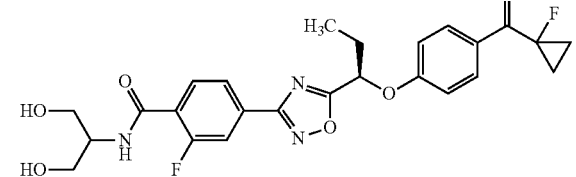

By using an N,N-dimethylformamide (1.0 mL) solution of the compound obtained in Reference Example 23 (67.0 mg, 0.156 mmol), N,N-dimethylformamide (1.0 mL), 1-hydroxybenzotriazole monohydrate (28.7 mg, 0.188 mmol), N-(3-dimethylaminopropyl)-N'-ethylcarbodiimide (36.0 mg, 0.188 mmol), and 2-amino-1,3-propanediol (57.0 mg, 0.626 mmol), the title compound (61.6 mg, yield: 79%) was obtained in the same manner as in Example 1. However, purification was performed by silica gel column chromatography (dichloromethane:methanol=100:0→90:10, v/v).
¹H-NMR (500 MHz, CDCl₃) δ ppm:
8.21 (1H, t, J=8 Hz), 8.04 (2H, dd, J=9, 2 Hz), 7.99 (1H, dd, J=8, 1 Hz), 7.87 (1H, dd, J=12, 1 Hz), 7.54-7.47 (1H, m), 7.04 (2H, d, J=9 Hz), 5.54 (1H, dd, J=7, 6 Hz), 4.28-4.21 (1H, m), 4.04-3.90 (4H, m), 2.40 (2H, dd, J=6, 4 Hz), 2.36-2.20 (2H, m), 1.56-1.50 (2H, m), 1.49-1.39 (1H, m), 1.15 (3H, t, J=7 Hz);
MS (ES) m/z: 502 [M+H]⁺.

Example 15

2-Fluoro-N-[(1R)-2-hydroxy-1-methylethyl]-4-{5-[(1R)-1-(4-isobutyrylphenoxy)propyl]-1,2,4-oxadiazol-3-yl}benzamide

[Chemical Formula 44]

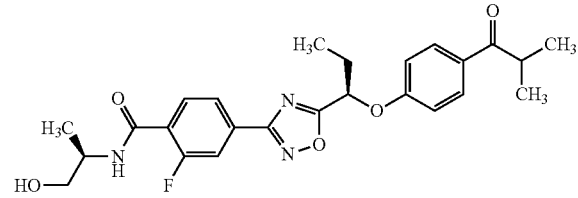

By using the compound obtained in Reference Example 25 (100 mg, 0.242 mmol), N,N-dimethylformamide (1.2 mL), 1-hydroxybenzotriazole monohydrate (44.6 mg, 0.291 mmol), N-(3-dimethylaminopropyl)-N'-ethylcarbodiimide (55.8 mg, 0.291 mmol), and (R)-2-amino-1-propanol (56.3 □L, 0.727 mmol), the title compound (101 mg, yield: 89%) was obtained in the same manner as in Example 1. However, purification was performed by silica gel column chromatography (hexane:ethyl acetate=70:30→0:100, v/v).

¹H-NMR (500 MHz, CDCl₃) δ ppm:
8.20 (1H, t, J=8 Hz), 7.98 (1H, dd, J=8, 2 Hz), 7.93 (2H, d, J=9 Hz), 7.85 (1H, dd, J=13, 2 Hz), 7.03 (2H, d, J=9 Hz), 6.95-6.85 (1H, m), 5.51 (1H, dd, J=7, 6 Hz), 4.38-4.29 (1H, m), 3.84-3.77 (1H, m), 3.72-3.65 (1H, m), 3.53-3.43 (1H, m), 2.44 (1H, dd, J=6, 5 Hz), 2.36-2.18 (2H, m), 1.32 (3H, d, J=7 Hz), 1.18 (6H, dd, J=7, 2 Hz), 1.14 (3H, t, J=7 Hz);

MS (ES) m/z: 470 [M+H]⁺.

Example 16

2-Fluoro-N-[2-hydroxy-1-(hydroxymethyl)ethyl]-4-{5-[(1R)-1-(isobutyrylphenoxy)propyl]-1,2,4-oxadiazol-3-yl}benzamide

[Chemical Formula 45]

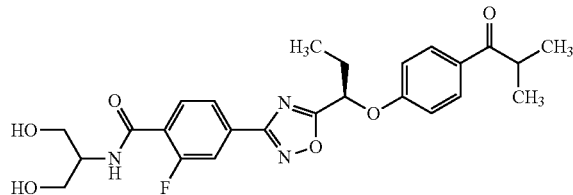

By using an N,N-dimethylformamide (1.0 mL) solution of the compound obtained in Reference Example 25 (118 mg, 0.286 mmol), N,N-dimethylformamide (1.4 mL), 1-hydroxybenzotriazole monohydrate (52.6 mg, 0.343 mmol), N-(3-dimethylaminopropyl)-N'-ethylcarbodiimide (65.8 mg, 0.343 mmol), and 2-amino-1,3-propanediol (78.2 mg, 0.858 mmol), the title compound (121 mg, yield: 87%) was obtained in the same manner as in Example 1. However, purification was performed by silica gel column chromatography (dichloromethane:methanol=100:0□90:10, v/v).

¹H-NMR (500 MHz, CDCl₃) δ ppm:
8.20 (1H, t, J=8 Hz), 7.98 (1H, dd, J=8, 2 Hz), 7.93 (2H, d, J=9 Hz), 7.86 (1H, dd, J=12, 2 Hz), 7.54-7.46 (1H, m), 7.03 (2H, d, J=9 Hz), 5.51 (1H, dd, J=7, 6 Hz), 4.28-4.19 (1H, m), 4.04-3.87 (4H, m), 3.53-3.43 (1H, m), 2.50 (2H, s), 2.36-2.18 (2H, m), 1.18 (6H, dd, J=7, 2 Hz), 1.14 (3H, t, J=7 Hz);

MS (ES) m/z: 486 [M+H]⁺.

Example 17

4-(5-{(1R)-1-[4-(Cyclopropylcarbonyl)phenoxy]propyl}-1,2,4-oxadiazol-3-yl)-2-fluoro-N-[(1S)-3-hydroxy-1-(hydroxymethyl)propyl]benzamide

[Chemical Formula 46]

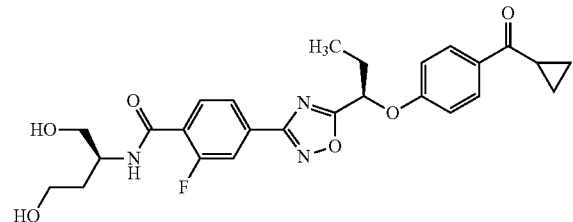

1-Hydroxybenzotriazole monohydrate (44.8 mg, 0.292 mmol) and N-(3-dimethylaminopropyl)-N'-ethylcarbodiimide (56.1 mg, 0.292 mmol) were added to an N,N-dimethylformamide (1.2 mL) solution of the compound obtained in Reference Example 8 (100 mg, 0.244 mmol) at room temperature, and the mixture was stirred at the same temperature for 30 minutes. Subsequently, an N,N-dimethylformamide (1.0 mL) solution of (2S)-2-amino-1,4-butanediol (Bioorg. Med. Chem. Lett. 2007, 17, 2086-2090.) (76.8 mg, 0.731 mmol) was added at 0° C., and the mixture was further stirred at the same temperature for 30 minutes. Water was added to the reaction mixture, and the mixture was subjected to extraction twice with ethyl acetate. The organic layer thus obtained was washed with a saturated aqueous solution of sodium hydrogen carbonate and brine, and then was dried over anhydrous sodium sulfate. The solvent was distilled off under reduced pressure, and the resulting residue was purified by silica gel column chromatography (dichloromethane: methanol=100:0→90:10, v/v) to give the title compound (100 mg, yield: 83%).

¹H-NMR (500 MHz, CDCl₃) δ ppm:
8.19 (1H, t, J=8 Hz), 8.01-7.96 (3H, m), 7.85 (1H, dd, J=12, 1 Hz), 7.43-7.36 (1H, m), 7.04 (2H, d, J=9 Hz), 5.53 (1H, dd, J=7, 6 Hz), 4.43 (1H, s), 3.91-3.66 (4H, m), 3.20-3.13 (1H, m), 2.65-2.56 (2H, m), 2.36-2.19 (2H, m), 2.02-1.93 (1H, m), 1.87-1.79 (1H, m), 1.22-1.17 (2H, m), 1.15 (3H, t, J=7 Hz), 1.02-0.97 (2H, m).

MS (FAB⁺) m/z: 498 [M+H]⁺.

Example 18

4-(5-{(1R)-1-[4-(Cyclopropylcarbonyl)phenoxy]ethyl}-1,2,4-oxadiazol-3-yl)-N-[(1r,3R,4S)-3,4-dihydroxycyclopentyl]-2-fluorobenzamide, and 4-(5-{(1R)-1-[4-(cyclopropylcarbonyl)phenoxy]ethyl}-1,2,4-oxadiazol-3-yl)-N-[(1s,3R,4S)-3,4-dihydroxycyclopentyl]-2-fluorobenzamide

[Chemical Formula 47]

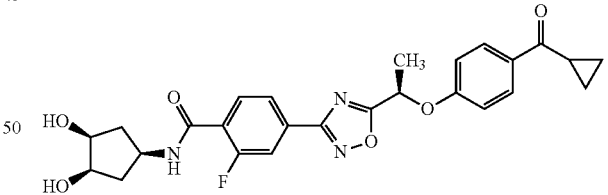

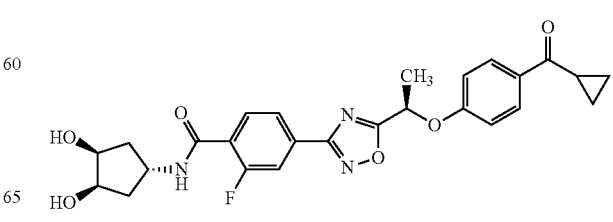

N-Methylmorpholine oxide (84.3 mg, 698 mmol) and osmium tetroxide (2.5 wt % tert-butanol solution, 219 μL, 17.5 μmol) were added to a tert-butanol/tetrahydrofuran/water (2:2:1, v/v) (5 mL) solution of the compound obtained in Reference Example 26 (161 mg, 349 μmol) at room temperature. The mixture was stirred at the same temperature for 20 minutes. Subsequently, a saturated aqueous solution of thiosulfuric acid was added to the reaction mixture, and the mixture was subjected to extraction three times with dichloromethane. The organic layer thus obtained was washed with water, and then was dried over anhydrous sodium sulfate. The solvent was distilled off under reduced pressure, and the resulting residue was purified by silica gel column chromatography (hexane:ethyl acetate=50:50→0:100, v/v) to give a mixture of the title compounds (78.4 mg, yield: 45%).

¹H-NMR (400 MHz, CDCl₃) δ ppm:
8.19 (1H, t, J=8 Hz), 8.05-7.92 (2H, m), 7.84 (1H, d, J=13 Hz), 7.55-7.45 (1H, m), 7.05 (2H, d, J=8 Hz), 6.77-6.70 (1H, m), 5.75 (1H, q, J=7 Hz), 4.77-4.67 (⅔H, m), 4.48-4.38 (⅓H, m), 4.35-4.27 (⅔H, m), 4.16-4.09 (⅓H, m), 2.89 (⅓H, d, J=4 Hz), 2.63-2.57 (1H, m), 2.33 (⅔H, m), 1.95-1.85 (5H, m), 1.22-1.19 (2H, m), 0.98-1.04 (2H, m);
MS (FAB+) m/z: 496 [M+H]⁺.

When the above diastereomer mixture is separated, each diastereomer can be obtained by a method known in the pertinent art, for example, by subjecting the above mixture to chiral column chromatography.

Example 19

4-(5-{(1R)-1-[4-(Cyclopropylcarbonyl)phenoxy]propyl}-1,2,4-oxadiazol-3-yl)-N-[(1R,2R)-2,3-dihydroxy-1-methylpropyl]-2-fluorobenzamide

[Chemical Formula 48]

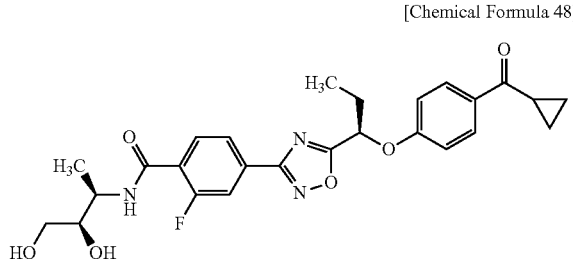 [SMILES: CC[C@@H](Oc1ccc(C(=O)C2CC2)cc1)c1nc(-c2ccc(C(=O)N[C@H](C)[C@@H](O)CO)c(F)c2)no1]

1-Hydroxybenzotriazole monohydrate (130 mg, 0.851 mmol) and N-(3-dimethylaminopropyl)-N'-ethylcarbodiimide (163 mg, 0.851 mmol) were added to an N,N-dimethylformamide (2.0 mL) solution of the compound obtained in Reference Example 8 (291 mg, 0.709 mmol) at room temperature, and the mixture was stirred at the same temperature for 30 minutes. Subsequently, triethylamine (297 μL, 2.13 mmol) was added to an N,N-dimethylformamide (2.0 mL) solution of the compound obtained in Reference Example 27 (350 mg) at room temperature, and the mixture was stirred for 10 minutes, and then the reaction mixture prepared previously was added, and the mixture was further stirred at the same temperature for 30 minutes. Water was added to the reaction mixture, and the mixture was subjected to extraction twice with ethyl acetate. The organic layer thus obtained was washed with a saturated aqueous solution of sodium hydrogen carbonate and brine, and then was dried over anhydrous sodium sulfate. The solvent was distilled off under reduced pressure, and the resulting residue was purified by silica gel column chromatography (dichloromethane:ethyl acetate=50:50→0:100, v/v) to give the title compound (293 g, yield: 83%).

¹H-NMR (500 MHz, CDCl₃) δ ppm:
8.19 (1H, t, J=8 Hz), 8.02-7.97 (3H, m), 7.87 (1H, dd, J=13, 1 Hz), 7.04 (2H, d, J=9 Hz), 6.92-6.86 (1H, m), 5.53 (1H, dd, J=7, 6 Hz), 4.28-4.19 (1H, m), 3.74-3.64 (2H, m), 3.53-3.46 (1H, m), 3.15 (1H, dd, J=9, 5 Hz), 2.78 (1H, d, J=8 Hz), 2.63-2.57 (1H, m), 2.35-2.19 (2H, m), 1.41 (3H, d, J=7 Hz), 1.22-1.18 (2H, m), 1.15 (3H, t, J=7 Hz), 1.02-0.98 (2H, m).
MS (FAB⁺) m/z: 498 [M+H]⁺.

Example 20

4-(5-{(1R)-1-[4-(Cyclopropylcarbonyl)phenoxy]propyl}-1,2,4-oxadiazol-3-yl)-N-[(1R,2S,3R)-2,3-dihydroxycyclopentyl]-2-fluorobenzamide, and 4-(5-{(1R)-1-[4-(cyclopropylcarbonyl)phenoxy]propyl}-1,2,4-oxadiazol-3-yl)-N-[(1S,2R,3S)-2,3-dihydroxycyclopentyl]-2-fluorobenzamide

[Chemical Formula 49]

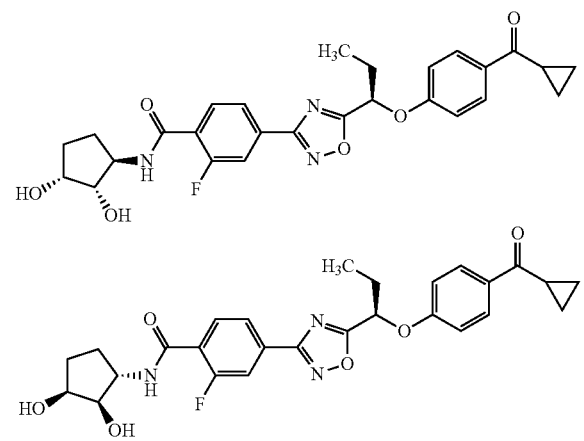

Triethylamine (0.340 mL, 2.44 mmol) was added to an N,N-dimethylformamide (5.0 mL) solution of the compound obtained in Reference Example 8 (250 mg, 0.609 mmol), N-(3-dimethylaminopropyl)-N'-ethylcarbodiimide (234 mg, 1.22 mmol), 1-Hydroxybenzotriazole monohydrate (93.3 mg, 0.609 mmol), and (1RS,2SR,3RS)-3-aminocyclopentane-1,2-diol hydrochloride (J. Org. Chem. 2009, 74, 6735-6748.) (140 mg, 0.914 mmol) at room temperature, and the mixture was stirred at the same temperature for 71 hours. Water was added to the reaction mixture, and the mixture was subjected to extraction with ethyl acetate. The organic layer thus obtained was washed with water, and then was dried over anhydrous sodium sulfate. The solvent was distilled off under reduced pressure, and the resulting residue was purified by silica gel thin layer chromatography (ethyl acetate) to give a mixture of the title compounds (134 mg, yield: 43%).

¹H-NMR (400 MHz, CDCl₃) δ ppm:
8.22 (1H, t, J=8 Hz), 8.02-7.98 (3H, m), 7.88 (1H, dd, J=13, 1 Hz), 7.06-7.02 (2H, m), 6.99-6.95 (1H, m), 5.55-5.51 (1H, m), 4.39-4.31 (1H, m), 4.20-4.18 (1H, m), 3.96-3.93 (1H, m), 2.63-2.56 (1H, m), 2.51-2.42 (1H, m), 2.35-2.21 (2H, m), 2.11-2.02 (1H, m), 1.96-1.88 (1H, m), 1.62-1.53 (1H, m), 1.22-1.18 (2H, m), 1.15 (3H, t, J=7 Hz), 1.02-0.98 (2H, m);
MS (ESI⁺) m/z: 510 [M+H]⁺.

When the above diastereomer mixture is separated, each diastereomer can be obtained by a method known in the pertinent art, for example, by subjecting the above mixture to chiral column chromatography.

Example 21

4-(5-{(1R)-1-[4-(Cyclopropylcarbonyl)phenoxy]ethyl}-1,2,4-oxadiazol-3-yl)-N-[(1R,2S,3R)-2,3-dihydroxycyclopentyl]-2-fluorobenzamide, and 4-(5-{(1R)-1-[4-(cyclopropylcarbonyl)phenoxy]ethyl}-1,2,4-oxadiazol-3-yl)-N-[(1S,2R,3S)-2,3-dihydroxycyclopentyl]-2-fluorobenzamide

[Chemical Formula 50]

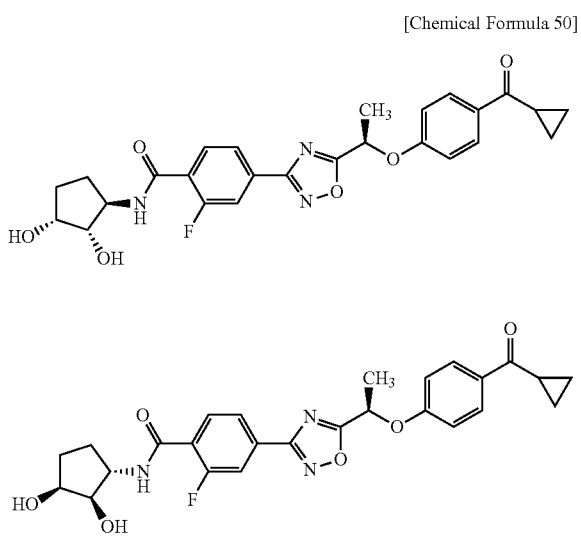

Triethylamine (0.633 mL, 4.54 mmol) was added to an N,N-dimethylformamide (6.0 mL) solution of the compound obtained in Reference Example 11 (300 mg, 0.757 mmol), N-(3-dimethylaminopropyl)-N'-ethylcarbodiimide (290 mg, 1.51 mmol), 1-Hydroxybenzotriazole monohydrate (116 mg, 0.757 mmol), and (1RS,2SR,3RS)-3-aminocyclopentane-1,2-diol hydrochloride (J. Org. Chem. 2009, 74, 6735-6748.) (174 mg, 1.14 mmol) at room temperature, and the mixture was stirred at the same temperature for 19 hours. Water was added to the reaction mixture, and the mixture was subjected to extraction with ethyl acetate. The organic layer thus obtained was washed with water, and then was dried over anhydrous sodium sulfate. The solvent was distilled off under reduced pressure, and the resulting residue was purified by silica gel thin layer chromatography (ethyl acetate) to give a mixture of the title compounds (132 mg, yield: 35%).

$^1$H-NMR (500 MHz, CDCl$_3$) δ ppm:

8.22 (1H, t, J=8 Hz), 8.02-7.99 (3H, m), 7.88 (1H, dd, J=13, 1 Hz), 7.07-7.03 (2H, m), 6.99-6.95 (1H, m), 5.76 (1H, q, J=7 Hz), 4.39-4.31 (1H, m), 4.20-4.18 (1H, m), 3.96-3.93 (1H, m), 2.63-2.57 (1H, m), 2.52-2.42 (1H, m), 2.11-2.02 (1H, m), 1.96-1.88 (1H, m), 1.92 (3H, d, J=7 Hz), 1.62-1.53 (1H, m), 1.22-1.19 (2H, m), 1.03-0.98 (2H, m);

MS (ESI$^+$) m/z: 496 [M+H]$^+$.

When the above diastereomer mixture is separated, each diastereomer can be obtained by a method known in the pertinent art, for example, by subjecting the above mixture to chiral column chromatography.

Example 22

4-(5-{(1R)-1-[4-(Cyclopropylcarbonyl)phenoxy]ethyl}-1,2,4-oxadiazol-3-yl)-N-[(3S,4S)-3,4-dihydroxycyclopentyl]-2-fluorobenzamide, and 4-(5-{(1R)-1-[4-(cyclopropylcarbonyl)phenoxy]ethyl}-1,2,4-oxadiazol-3-yl)-N-[(3R,4R)-3,4-dihydroxycyclopentyl]-2-fluorobenzamide

[Chemical Formula 51]

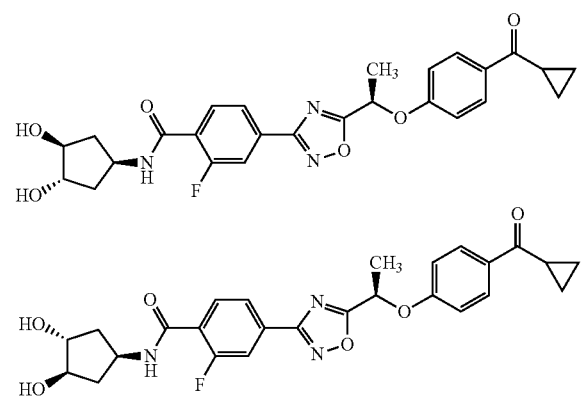

1-Hydroxybenzotriazole monohydrate (128 mg, 834 μmol) and N-(3-dimethylaminopropyl)-N'-ethylcarbodiimide (240 mg, 1.25 mmol) were added to an N,N-dimethylformamide (4 mL) solution of the compound obtained in Reference Example 11 (330 mg, 834 μmol) at room temperature, and the mixture was stirred at the same temperature for 30 minutes.

(1RS,2RS)-4-Amino-3-cyclopentane-1,2-diol (J. Med. Chem. 1992, 35, 2191-2195.) (115 mg, 1.00 mmol) was added, and the mixture was further stirred at the same temperature for 30 minutes. Water was added to the reaction mixture, and the mixture was subjected to extraction three times with ethyl acetate. The organic layer thus obtained was washed with a saturated aqueous solution of sodium hydrogen carbonate and a 10% aqueous solution of sodium chloride, and then was dried over anhydrous sodium sulfate. The solvent was distilled off under reduced pressure, and the resulting residue was purified by silica gel column chromatography (hexane:ethyl acetate=50:50→0:100, v/v) to give a mixture of the title compounds (218 mg, yield: 53%).

$^1$H-NMR (400 MHz, CDCl$_3$) δ ppm:

8.18 (1H, t, J=8 Hz), 8.02-7.95 (3H, m), 7.83 (1H, d, J=12 Hz), 7.33-7.26 (1H, m), 7.04 (2H, d, J=9 Hz), 5.75 (1H, q, J=7 Hz), 4.69-4.59 (1H, m), 4.29 (1H, br s), 4.16 (1H, br s), 3.04 (1H, d, J=5 Hz), 2.63-2.51 (2H, m), 2.29 (1H, dt, J=14, 6 Hz), 2.14 (1H, ddd, J=14, 8, 2 Hz), 1.91 (3H, d, J=7 Hz), 1.84-1.77 (1H, m), 1.74 (1H, d, J=2 Hz), 1.22-1.16 (2H, m), 1.04-0.98 (2H, m); MS (FAB$^+$) m/z: 496 [M+H]$^+$.

When the above diastereomer mixture is separated, each diastereomer can be obtained by a method known in the pertinent art, for example, by subjecting the above mixture to chiral column chromatography.

Example 23

4-(5-{(1R)-1-[4-(Cyclopropylcarbonyl)phenoxy]ethyl}-1,2,4-oxadiazol-3-yl)-N-[(1R,2R)-2,3-dihydroxy-1-methylpropyl]-2-fluorobenzamide

[Chemical Formula 52]

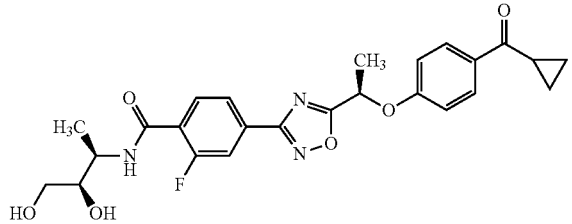

1-Hydroxybenzotriazole monohydrate (139 mg, 0.908 mmol) and N-(3-dimethylaminopropyl)-N'-ethylcarbodiimide (174 mg, 0.908 mmol) were added to an N,N-dimethylformamide (2.0 mL) solution of the compound obtained in Reference Example 8 (300 mg, 0.757 mmol) at room temperature, and the mixture was stirred at the same temperature for 30 minutes. Subsequently, triethylamine (316 μL, 2.27 mmol) was added to an N,N-dimethylformamide (2.0 mL) solution of the compound obtained in Reference Example 27 (354 mg) at room temperature, and the mixture was stirred for 10 minutes, and then the reaction mixture prepared previously was added, and the mixture was further stirred at the same temperature for 30 minutes. Water was added to the reaction mixture, and the mixture was subjected to extraction twice with ethyl acetate. The organic layer thus obtained was washed with a saturated aqueous solution of sodium hydrogen carbonate and brine, and then was dried over anhydrous sodium sulfate. The solvent was distilled off under reduced pressure, and the resulting residue was purified by silica gel column chromatography (dichloromethane:ethyl acetate=50:50→0:100, v/v) to give the title compound (335 mg, yield: 92%).

$^1$H-NMR (500 MHz, CDCl$_3$) δ ppm:
8.20 (1H, t, J=8 Hz), 8.01 (2H, d, J=9 Hz), 8.00 (1H, dd, J=8, 1 Hz), 7.87 (1H, dd, J=12, 1 Hz), 7.05 (2H, d, J=9 Hz), 6.93-6.86 (1H, m), 5.76 (1H, q, J=7 Hz), 4.28-4.19 (1H, m), 3.74-3.64 (2H, m), 3.51-3.45 (1H, m), 3.17 (1H, dd, J=8, 5 Hz), 2.80 (1H, dd, J=8, 4 Hz), 2.63-2.58 (1H, m), 1.92 (3H, d, J=7 Hz), 1.41 (3H, d, J=6 Hz), 1.23-1.18 (2H, m), 1.03-0.98 (2H, m).
MS (FAB$^+$) m/z: 484 [M+H]$^+$.

Production Example 1

4-(5-{(1R)-1-[4-(Cyclopropylcarbonyl)phenoxy]propyl}-1,2,4-oxadiazol-3-yl)-N-[(1R,2R,3S)-2,3-dihydroxycyclopentyl]-2-fluorobenzamide, and 4-(5-{(1R)-1-[4-(cyclopropylcarbonyl)phenoxy]propyl}-1,2,4-oxadiazol-3-yl)-N-[(1S,2S,3R)-2,3-dihydroxycyclopentyl]-2-fluorobenzamide

[Chemical Formula 53]

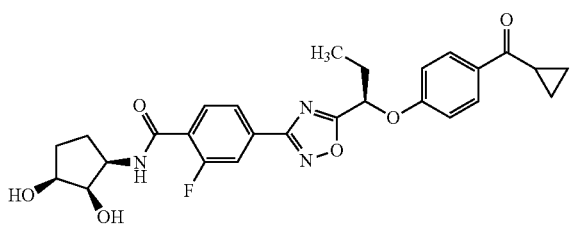

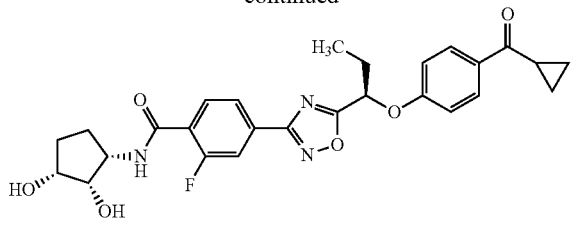

By using the compound obtained in Reference Example 8, and (1RS,2SR,3SR)-3-aminocyclopentane-1,2-diol hydrochloride (J. Org. Chem. 2009, 74, 6735-6748.), a mixture of the title compounds can be obtained in the same manner as in Example 20.

When the above diastereomer mixture is separated, each diastereomer can be obtained by a method known in the pertinent art, for example, by subjecting the above mixture to chiral column chromatography.

Production Example 2

4-(5-{(1R)-1-[4-(Cyclopropylcarbonyl)phenoxy]ethyl}-1,2,4-oxadiazol-3-yl)-N-[(1R,2R,3S)-2,3-dihydroxycyclopentyl]-2-fluorobenzamide, and 4-(5-{(1R)-1-[4-(cyclopropylcarbonyl)phenoxy]ethyl}-1,2,4-oxadiazol-3-yl)-N-[(1S,2S,3R)-2,3-dihydroxycyclopentyl]-2-fluorobenzamide

[Chemical Formula 54]

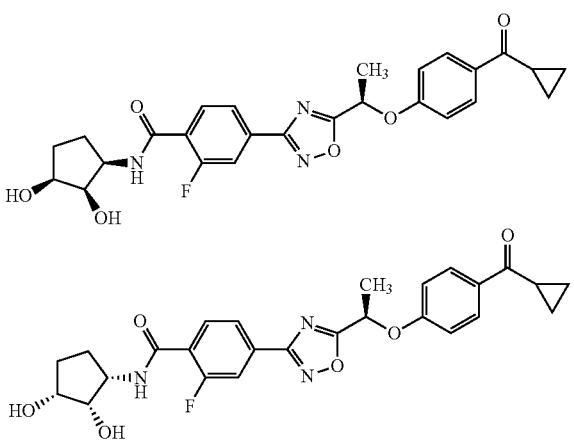

By using the compound obtained in Reference Example 11, and (1RS,2SR,3SR)-3-aminocyclopentane-1,2-diol hydrochloride (J. Org. Chem. 2009, 74, 6735-6748.), a mixture of the title compounds can be obtained in the same manner as in Example 21.

When the above diastereomer mixture is separated, each diastereomer can be obtained by a method known in the pertinent art, for example, by subjecting the above mixture to chiral column chromatography.

Formulation Example 5 g of each of the compounds obtained in the Examples, 90 g of lactose, 34 g of corn starch, 20 g of crystalline cellulose, and 1 g of magnesium stearate are mixed with a blender, and then the mixture is tableted with a tableting machine. Thereby, tablets are obtained.

Test Example 1

Mouse oGTT (Oral Glucose Tolerance Test)

A dosing preparation (1 mg/mL of each compound) was produced by suspending in a 0.5 w/v % methyl cellulose solution and then grinding in an agate mortar. Male C57/BL6J mice (Charles River Laboratories Japan, Inc.) were purchased at 6 to 8 weeks of age, and then used at 9 to 13 weeks of age. The mice were fasted from the hours of 17:00 to 18:00 on one day before the test day, and the test was started after 16 to 17 hours-fasting. Five mice were used for each group. Before dosing a compound, blood was collected from the tail vein. Thereafter, a suspension of the compound was orally administered at a dosage of 10 mg/kg. The 0.5 w/v % methyl cellulose solution was administered to a negative control group. Twenty five minutes after dosing the compound, blood was collected from the tail vein, and then thirty minutes after dosing the compound, 30 w/v % glucose solution was orally administered at a volume of 10 mL/kg. Blood was collected from the tail vein 15, 30, 60 and 120 minutes after the glucose administration. Each of the blood samples was centrifuged to obtain the plasma, and the plasma glucose level (mg/dL) was measured with a glucose analyzer (Glucoloader GXT, A&T Corp.). The plasma glucose AUC (mg/dL min) in each mouse was calculated using the plasma glucose values at 5 minutes before and 15, 30, 60 and 120 minutes after the glucose administration. The arithmetic mean of the AUC value was calculated for each group and the percentage decrease in plasma glucose AUC (%) compared with the negative control group was calculated as an index of the efficacy.

As a result, the compounds of Examples 3 to 6, 8 to 19, 21, and 22 showed 5% to 20% percentage decrease in plasma glucose AUC (%) and the compounds of Examples 1, 2, 7, 20, and 23 showed more than 20% percentage decrease in plasma glucose AUC.

Test Example 2

Rat oGTT and Measurement of Plasma Compound Concentration

A dosing preparation (1 to 10 mg/mL of each compound) can be made up by suspending in a 0.5 w/v % methyl cellulose solution. To assess the dose dependency, the compound suspension is diluted with 0.5 w/v % methyl cellulose solution in a stepwise fashion. Male Zucker fatty rats (Charles River Laboratories Japan, Inc.) can be used at 10 to 18 weeks of age. Two days before the oGTT, body weights, plasma glucose and plasma insulin levels are measured, and rats are equally allocated to each group (n=5 to 8) based on these parameters. The rats are fasted from around 15:00 on one day before the oGTT day. On the oGTT day, the dosing preparation is orally administered to the rats at a volume of 1 to 5 mL/kg, and 30 minutes after dosing, a 25 to 50 w/v % glucose solution is orally administered at a volume of 4 mL/kg. Blood is collected from the tail vein before dosing the compound, 5 minutes before the administration of glucose, and 30, 60, 120, and 180 minutes after the administration of glucose. The obtained blood is centrifuged to separate the plasma, and the plasma glucose level is measured with a glucose analyzer (Glucoloader GXT, A&T Corp.). The plasma glucose AUC in each rat after the administration of glucose is calculated. The percentage decrease in plasma glucose AUC (%) compared with the vehicle-administrated group can be expressed as the efficacy of the compound.

The plasma sample obtained by the method described above can be used for measurement of the plasma concentration of the test compound. In order to quantify the plasma concentration of the test compound, blood is collected 4 to 8 hours after the administration, and even 24 hours after the administration. The plasma is subjected to protein removal, and can be applied to a liquid chromatography/mass analyzer to quantify the plasma concentration of the test compound.

Test Example 3

Assessment for the Protective Effect on Pancreatic β Cells

The protective effect of the test compound on pancreatic β cells can be confirmed by making reference to the method described in Junko Ogawa, et al., Life Sciences, Vol. 65, No. 12, pp. 1287-1296 (1999).

INDUSTRIAL APPLICABILITY

The compound of the present invention or a pharmaceutically acceptable salt thereof is capable of treating and/or preventing type 1 diabetes, type 2 diabetes, gestational diabetes, hyperglycemia due to other factors, impaired glucose tolerance, diabetes-associated diseases, diabetic complications and the like, and is therefore useful as an active ingredient of a pharmaceutical composition for protecting β cells or the pancreas.

The invention claimed is:
1. A compound represented by general formula (I):

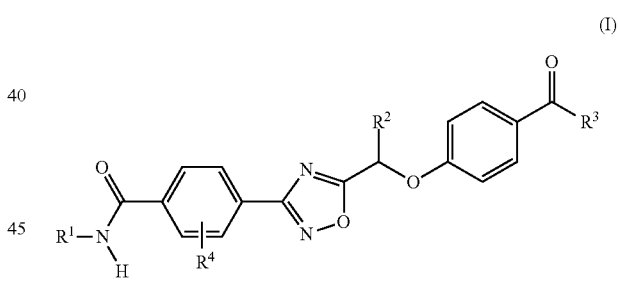

or a pharmaceutically acceptable salt thereof,
wherein $R^1$ is a hydroxy C1-C6 alkyl group or a hydroxy C3-C6 cycloalkyl group, each of which may be substituted with 1 to 3 substituents selected from substituent subgroup α,
substituent subgroup α is a group consisting of a hydroxyl group and a carbamoyl group,
$R^2$ is a methyl group or an ethyl group,
$R^3$ is a C1-C6 alkyl group or a C3-C6 cycloalkyl group, each of which may be substituted with 1 to 3 halogen atoms, and
$R^4$ is a halogen atom.

2. The compound of claim 1, wherein $R^1$ is a hydroxy C1-C3 alkyl group or a hydroxy C3-C4 cycloalkyl group, each of which may be substituted with 1 to 3 substituents selected from substituent subgroup α.

3. The compound of claim 1, wherein $R^1$ is selected from the group consisting of a hydroxyethyl group, a hydroxypropyl group, a hydroxyisopropyl group, and a hydroxycyclopentyl group, each of which may be substituted with one substituent selected from substituent subgroup α.

4. The compound of claim 1, wherein $R^3$ is a C1-C4 alkyl group or a C3-C4 cycloalkyl group, each of which may be substituted with 1 to 3 halogen atoms.

5. The compound of claim 1, wherein $R^3$ is selected from the group consisting of an isopropyl group, a tert-butyl group, a cyclopropyl group, and a cyclobutyl group, each of which may be substituted with one halogen atom.

6. The compound of claim 1, wherein $R^4$ is a fluorine atom.

7. The compound of claim 1 or a pharmaceutically acceptable salt thereof, wherein the compound is selected from the group consisting of:
- 4-(5-{(1R)-1-[4-(cyclopropylcarbonyl)phenoxy]propyl}-1,2,4-oxadiazol-3-yl)-N-[(2S)-2,3-dihydroxypropyl]-2-fluorobenzamide;
- N-[(1S)-2-amino-1-(hydroxymethyl)-2-oxoethyl]-4-(5-{(1R)-1-[4-(cyclopropylcarbonyl)phenoxy]propyl}-1,2,4-oxadiazol-3-yl)-2-fluorobenzamide;
- 4-(5-{(1R)-1-[4-(cyclopropylcarbonyl)phenoxy]propyl}-1,2,4-oxadiazol-3-yl)-2-fluoro-N-[(1R)-2-hydroxy-1-methylethyl]benzamide;
- 4-(5-{(1R)-1-[4-(cyclopropylcarbonyl)phenoxy]propyl}-1,2,4-oxadiazol-3-yl)-2-fluoro-N-[(1S)-2-hydroxy-1-methylethyl]benzamide;
- 4-(5-{(1R)-1-[4-(cyclopropylcarbonyl)phenoxy]propyl}-1,2,4-oxadiazol-3-yl)-N-[(2R)-2,3-dihydroxypropyl]-2-fluorobenzamide;
- 4-(5-{(1R)-1-[4-(cyclopropylcarbonyl)phenoxy]propyl}-1,2,4-oxadiazol-3-yl)-2-fluoro-N-[2-hydroxy-1-(hydroxymethyl)ethyl]benzamide;
- 4-(5-{(1R)-1-[4-(cyclopropylcarbonyl)phenoxy]ethyl}-1,2,4-oxadiazol-3-yl)-2-fluoro-N-[2-hydroxy-1-(hydroxymethyl)ethyl]benzamide;
- 4-(5-{(1R)-1-[4-(cyclopropylcarbonyl)phenoxy]ethyl}-1,2,4-oxadiazol-3-yl)-2-fluoro-N-[(1S)-2-hydroxy-1-methylethyl]benzamide;
- 4-(5-{(1R)-1-[4-(cyclopropylcarbonyl)phenoxy]ethyl}-1,2,4-oxadiazol-3-yl)-2-fluoro-N-[(1R,2R)-2-hydroxycyclopentyl]benzamide;
- 4-(5-{(1R)-1-[4-(cyclopropylcarbonyl)phenoxy]ethyl}-1,2,4-oxadiazol-3-yl)-2-fluoro-N-[(1R)-2-hydroxy-1-methylethyl]benzamide;
- 4-(5-{(1R)-1-[4-(cyclopropylcarbonyl)phenoxy]ethyl}-1,2,4-oxadiazol-3-yl)-2-fluoro-N-[(1S,2S)-2-hydroxycyclopentyl]benzamide;
- 4-(5-{(1R)-1-[4-(2,2-dimethylpropanoyl)phenoxy]propyl}-1,2,4-oxadiazol-3-yl)-2-fluoro-N-[2-hydroxy-1-(hydroxymethyl)ethyl]benzamide;
- 4-(5-{(1R)-1-[4-(cyclobutylcarbonyl)phenoxy]propyl}-1,2,4-oxadiazol-3-yl)-2-fluoro-N-[2-hydroxy-1-(hydroxymethyl)ethyl]benzamide;
- 2-fluoro-4-{5-[(1R)-1-{4-[(1-fluorocyclopropyl)carbonyl]phenoxy}propyl]-1,2,4-oxadiazol-3-yl}-N-[2-hydroxy-1-(hydroxymethyl)ethyl]benzamide;
- 2-fluoro-N-[(1R)-2-hydroxy-1-methylethyl]-4-{5-[(1R)-1-(4-isobutyrylphenoxy)propyl]-1,2,4-oxadiazol-3-yl}benzamide; and
- 2-fluoro-N-[2-hydroxy-1-(hydroxymethyl)ethyl]-4-{5-[(1R)-1-(isobutyrylphenoxy)propyl]-1,2,4-oxadiazol-3-yl}benzamide.

8. The compound of claim 7 or a pharmaceutically acceptable salt thereof, wherein the compound is 4-(5-{(1R)-1-[4-(Cyclopropylcarbonyl)phenoxy]propyl}-1,2,4-oxadiazol-3-yl)-N-[(2S)-2,3-dihydroxypropyl]-2-fluorobenzamide.

9. The compound of claim 7 or a pharmaceutically acceptable salt thereof, wherein the compound is N-[(1S)-2-Amino-1-(hydroxymethyl)-2-oxoethyl]-4-(5-{(1R)-1-[4-(cyclopropylcarbonyl)phenoxy]propyl}-1,2,4-oxadiazol-3-yl)-2-fluorobenzamide.

10. The compound of claim 7 or a pharmaceutically acceptable salt thereof, wherein the compound is 4-(5-{(1R)-1-[4-(Cyclopropylcarbonyl)phenoxy]propyl}-1,2,4-oxadiazol-3-yl)-2-fluoro-N-[(1R)-2-hydroxy-1-methylethyl]benzamide.

11. The compound of claim 7 or a pharmaceutically acceptable salt thereof, wherein the compound is 4-(5-{(1R)-1-[4-(Cyclopropylcarbonyl)phenoxy]propyl}-1,2,4-oxadiazol-3-yl)-2-fluoro-N-[(1S)-2-hydroxy-1-methylethyl]benzamide.

12. The compound of claim 7 or a pharmaceutically acceptable salt thereof, wherein the compound is 4-(5-{(1R)-1-[4-(Cyclopropylcarbonyl)phenoxy]propyl}-1,2,4-oxadiazol-3-yl)-N-[(2R)-2,3-dihydroxypropyl]-2-fluorobenzamide.

13. The compound of claim 7 or a pharmaceutically acceptable salt thereof, wherein the compound is 4-(5-{(1R)-1-[4-(Cyclopropylcarbonyl)phenoxy]propyl}-1,2,4-oxadiazol-3-yl)-2-fluoro-N-[2-hydroxy-1-(hydroxymethyl)ethyl]benzamide.

14. The compound of claim 7 or a pharmaceutically acceptable salt thereof, wherein the compound is 4-(5-{(1R)-1-[4-(Cyclopropylcarbonyl)phenoxy]ethyl}-1,2,4-oxadiazol-3-yl)-2-fluoro-N-[2-hydroxy-1-(hydroxymethyl)ethyl]benzamide.

15. The compound of claim 7 or a pharmaceutically acceptable salt thereof, wherein the compound is 4-(5-{(1R)-1-[4-(Cyclopropylcarbonyl)phenoxy]ethyl}-1,2,4-oxadiazol-3-yl)-2-fluoro-N-[(1S)-2-hydroxy-1-methylethyl]benzamide.

16. The compound of claim 7 or a pharmaceutically acceptable salt thereof, wherein the compound is 4-(5-{(1R)-1-[4-(Cyclopropylcarbonyl)phenoxy]ethyl}-1,2,4-oxadiazol-3-yl)-2-fluoro-N-[(1R,2R)-2-hydroxycyclopentyl]benzamide.

17. The compound of claim 7 or a pharmaceutically acceptable salt thereof, wherein the compound is 4-(5-{(1R)-1-[4-(Cyclopropylcarbonyl)phenoxy]ethyl}-1,2,4-oxadiazol-3-yl)-2-fluoro-N-[(1R)-2-hydroxy-1-methylethyl]benzamide.

18. The compound of claim 7 or a pharmaceutically acceptable salt thereof, wherein the compound is 4-(5-{(1R)-1-[4-(Cyclopropylcarbonyl)phenoxy]ethyl}-1,2,4-oxadiazol-3-yl)-2-fluoro-N-[(1S,2S)-2-hydroxycyclopentyl]benzamide.

19. The compound of claim 7 or a pharmaceutically acceptable salt thereof, wherein the compound is 4-(5-{(1R)-1-[4-(2,2-Dimethylpropanoyl)phenoxy]propyl}-1,2,4-oxadiazol-3-yl)-2-fluoro-N-[2-hydroxy-1-(hydroxymethyl)ethyl]benzamide.

20. The compound of claim 7 or a pharmaceutically acceptable salt thereof, wherein the compound is 4-(5-{(1R)-1-[4-(Cyclobutylcarbonyl)phenoxy]propyl}-1,2,4-oxadiazol-3-yl)-2-fluoro-N-[2-hydroxy-1-(hydroxymethyl)ethyl]benzamide.

21. The compound of claim 7 or a pharmaceutically acceptable salt thereof, wherein the compound is 2-Fluoro-4-{5-[(1R)-1-{4-[(1-fluorocyclopropyl)carbonyl]phenoxy}propyl]-1,2,4-oxadiazol-3-yl}-N-[2-hydroxy-1-(hydroxymethyl)ethyl]benzamide.

22. The compound of claim 7 or a pharmaceutically acceptable salt thereof, wherein the compound is 2-Fluoro-N-[(1R)-2-hydroxy-1-methylethyl]-4-{5-[(1R)-1-(4-isobutyrylphenoxy)propyl]-1,2,4-oxadiazol-3-yl}benzamide.

23. The compound of claim 7 or a pharmaceutically acceptable salt thereof, wherein the compound is 2-Fluoro-N-[2-hydroxy-1-(hydroxymethyl)ethyl]-4-{5-[(1R)-1-(isobutyrylphenoxy)propyl]-1,2,4-oxadiazol-3-yl}benzamide.

24. A method of treating type 1 diabetes, type 2 diabetes, or obesity comprising administering to a mammal a compound of claim 7 or a pharmaceutically acceptable salt thereof.

25. The method of claim 24, wherein the mammal is a human.

26. A method of protecting β cells of the pancreas, comprising administering to a mammal a compound of claim 7 or a pharmaceutically acceptable salt thereof.

27. The method of claim 26, wherein the mammal is a human.

* * * * *